(12) United States Patent
Horikawa et al.

(10) Patent No.: US 11,350,879 B2
(45) Date of Patent: Jun. 7, 2022

(54) DEVICE AND METHOD FOR SEQUENTIAL POSTURE IDENTIFICATION AND AUTONOMIC FUNCTION INFORMATION ACQUISITION

(71) Applicant: NIPPON TELEGRAPH AND TELEPHONE CORPORATION, Chiyoda-ku (JP)

(72) Inventors: Keitaro Horikawa, Musashino (JP); Yoshitaka Nakamura, Musashino (JP); Masato Sawada, Musashino (JP); Akihiro Yamanaka, Musashino (JP); Shingo Tsukada, Atsugi (JP); Toshiya Yamada, Yokohama (JP)

(73) Assignee: NIPPON TELEGRAPH AND TELEPHONE CORPORATION, Chiyoda-ku (JP)

( * ) Notice: Subject to any disclaimer, the term of this patent is extended or adjusted under 35 U.S.C. 154(b) by 1331 days.

(21) Appl. No.: 15/551,331

(22) PCT Filed: Feb. 16, 2016

(86) PCT No.: PCT/JP2016/054438
§ 371 (c)(1),
(2) Date: Aug. 16, 2017

(87) PCT Pub. No.: WO2016/133088
PCT Pub. Date: Aug. 25, 2016

(65) Prior Publication Data
US 2018/0064397 A1    Mar. 8, 2018

(30) Foreign Application Priority Data
Feb. 17, 2015 (JP) .............................. JP2015-028850

(51) Int. Cl.
A61B 5/024 (2006.01)
A61B 5/00 (2006.01)
(Continued)

(52) U.S. Cl.
CPC .............. *A61B 5/721* (2013.01); *A61B 5/024* (2013.01); *A61B 5/02405* (2013.01);
(Continued)

(58) Field of Classification Search
CPC ........ G16H 20/60; G16H 20/30; G16H 40/67; G16H 10/60; G16H 50/20; G16H 15/00;
(Continued)

(56) References Cited

U.S. PATENT DOCUMENTS 8,866,606 B1 * 10/2014 Will .................... G08B 25/016
340/539.11
2005/0251054 A1   11/2005 Zhirnov et al.
(Continued)

FOREIGN PATENT DOCUMENTS

JP    2000-245713 A    9/2000
JP    2004-164282 A    6/2004
(Continued)

OTHER PUBLICATIONS

Akimitsu Akahori, et al., "A study of estimation of actions using a three-axis acceleration sensor", IEICE Technical Report, MBE, ME and Bio Cybernetics, The Institute of Electronics, Information and Communication Engineers, Dec. 2, 2005, vol. 105, No. 456, (with English translation), (17 pages).
(Continued)

*Primary Examiner* — Reginald R Reyes
(74) *Attorney, Agent, or Firm* — Oblon, McClelland, Maier & Neustadt, L.L.P.

(57) ABSTRACT

A wearable device attached to a subject includes an accelerometer that measures acceleration information, and a
(Continued)

biological sensor that measures biological signal information of the subject. From the measured acceleration information and biological signal information, first feature data corresponding to a first predetermined period and second feature data corresponding to a second predetermined period are extracted. By machine learning based on the first feature data, a dynamic/static activity identification model, a dynamic-activity identification model, and a static-activity identification model, for the subject, are generated. By combination of results of determination based on each of the identification models, a posture and an activity of the subject are identified, and correspondence information, which associates the identified posture and activity with the biological signal information of the subject, is generated.

10 Claims, 21 Drawing Sheets

(51) Int. Cl.
    *A61B 5/16*     (2006.01)
    *A61B 5/11*     (2006.01)
    *G16H 50/30*     (2018.01)
    *G16H 20/30*     (2018.01)
    *G16H 50/20*     (2018.01)
    *A61B 5/352*     (2021.01)
    *A61B 5/021*     (2006.01)

(52) U.S. Cl.
    CPC .......... *A61B 5/1116* (2013.01); *A61B 5/1118* (2013.01); *A61B 5/1123* (2013.01); *A61B 5/16* (2013.01); *A61B 5/4035* (2013.01); *A61B 5/7267* (2013.01); *A61B 5/7282* (2013.01); *G16H 20/30* (2018.01); *G16H 50/20* (2018.01); *G16H 50/30* (2018.01); *A61B 5/021* (2013.01); *A61B 5/352* (2021.01); *A61B 5/6804* (2013.01); *A61B 2503/10* (2013.01); *A61B 2503/12* (2013.01); *A61B 2505/09* (2013.01)

(58) Field of Classification Search
    CPC ........ G16H 20/10; G16H 20/70; G16H 50/70; G16H 70/40; G16H 20/17; G16H 40/63; G16H 50/30; G16H 70/20; G16H 80/00
    See application file for complete search history.

(56) References Cited

U.S. PATENT DOCUMENTS

| | | |
|---|---|---|
| 2005/0251055 A1 | 11/2005 | Zhirnov et al. |
| 2005/0251056 A1 | 11/2005 | Gribkov et al. |
| 2005/0251057 A1 | 11/2005 | Sanders et al. |
| 2005/0251424 A1 | 11/2005 | Sanders et al. |
| 2007/0066909 A1 | 3/2007 | Fendrock |
| 2008/0275349 A1 | 11/2008 | Halperin et al. |
| 2011/0054359 A1 | 3/2011 | Sazonov et al. |
| 2012/0132211 A1 | 5/2012 | Halperin et al. |
| 2012/0310050 A1 | 12/2012 | Osorio |
| 2013/0217979 A1 | 8/2013 | Blackadar et al. |
| 2013/0245486 A1 | 9/2013 | Simon et al. |
| 2014/0156043 A1 | 6/2014 | Blackadar et al. |
| 2014/0243613 A1 | 8/2014 | Osorio |
| 2015/0196246 A1 | 7/2015 | Osorio |
| 2016/0012197 A1* | 1/2016 | Eromo .................. G06Q 10/10 705/2 |
| 2016/0058359 A1 | 3/2016 | Osorio |
| 2016/0119293 A1* | 4/2016 | Leon .................. H04L 63/0442 713/168 |
| 2016/0151628 A1 | 6/2016 | Simon et al. |
| 2017/0079573 A1 | 3/2017 | Osorio |
| 2017/0316182 A1 | 11/2017 | Blackadar et al. |

FOREIGN PATENT DOCUMENTS

| | | |
|---|---|---|
| JP | 2005-21450 A | 1/2005 |
| JP | 2006-102265 A | 4/2006 |
| JP | 2007-14567 A | 1/2007 |
| JP | 2007-160076 A | 6/2007 |
| JP | 2007-209396 A | 8/2007 |
| JP | 2009-39466 A | 2/2009 |
| JP | 2009-507574 A | 2/2009 |
| JP | 2010-207488 A | 9/2010 |
| JP | 2011-45524 A | 3/2011 |
| JP | 2012-239666 A | 12/2012 |
| JP | 2013/038551 A1 | 3/2013 |
| WO | WO 2008/135985 A1 | 11/2008 |
| WO | WO 2010/096691 A2 | 8/2010 |
| WO | WO 2010/096691 A3 | 8/2010 |

OTHER PUBLICATIONS

International Search Report dated May 17, 2016 in PCT/JP2016/054438 filed Feb. 16, 2016.

Office Action dated Oct. 24, 2017 in Japanese Patent Application No. 2015-028850 (with unedited computer generated English translation).

Extended European Search Report dated Jan. 8, 2018 in Patent Application No. 16752474.3, 9 pages.

\* cited by examiner

FIG.3
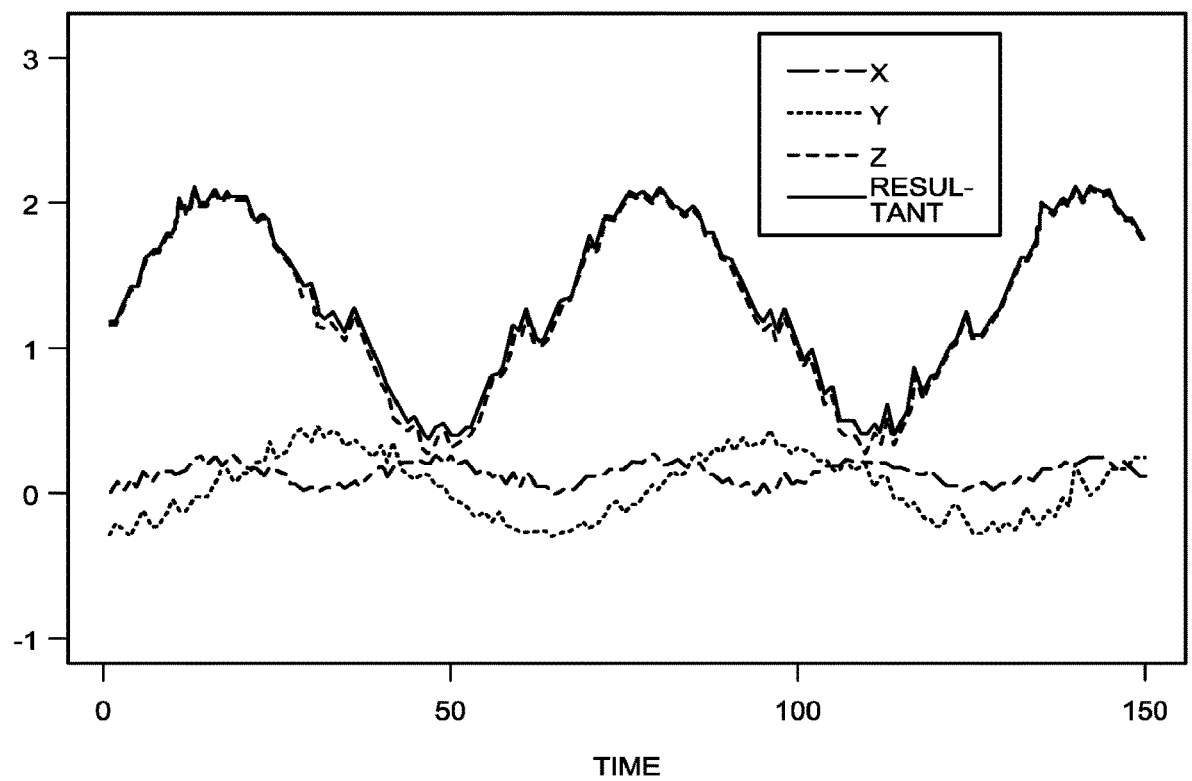
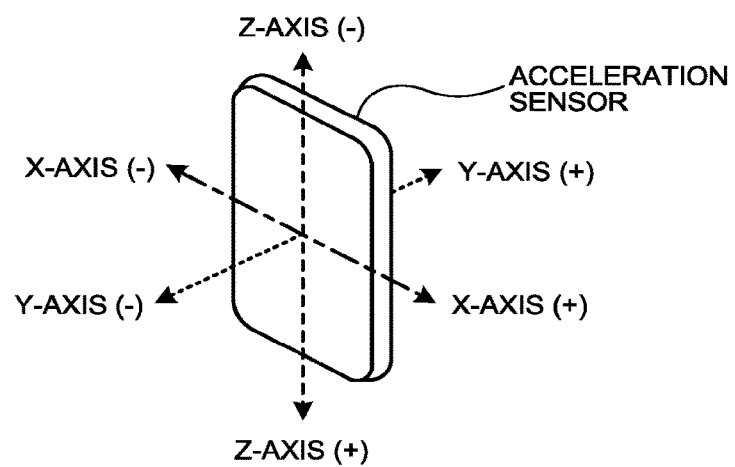

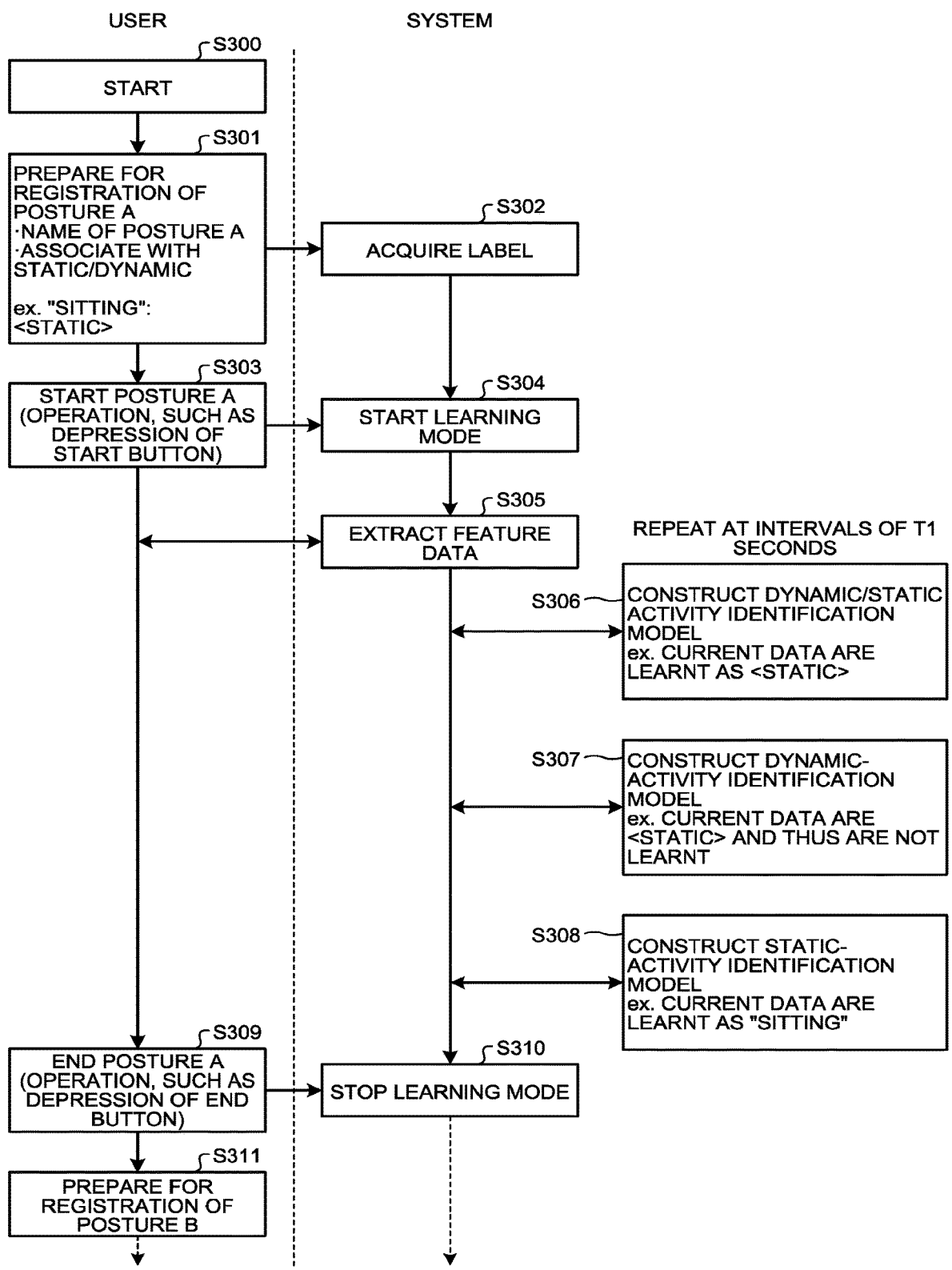

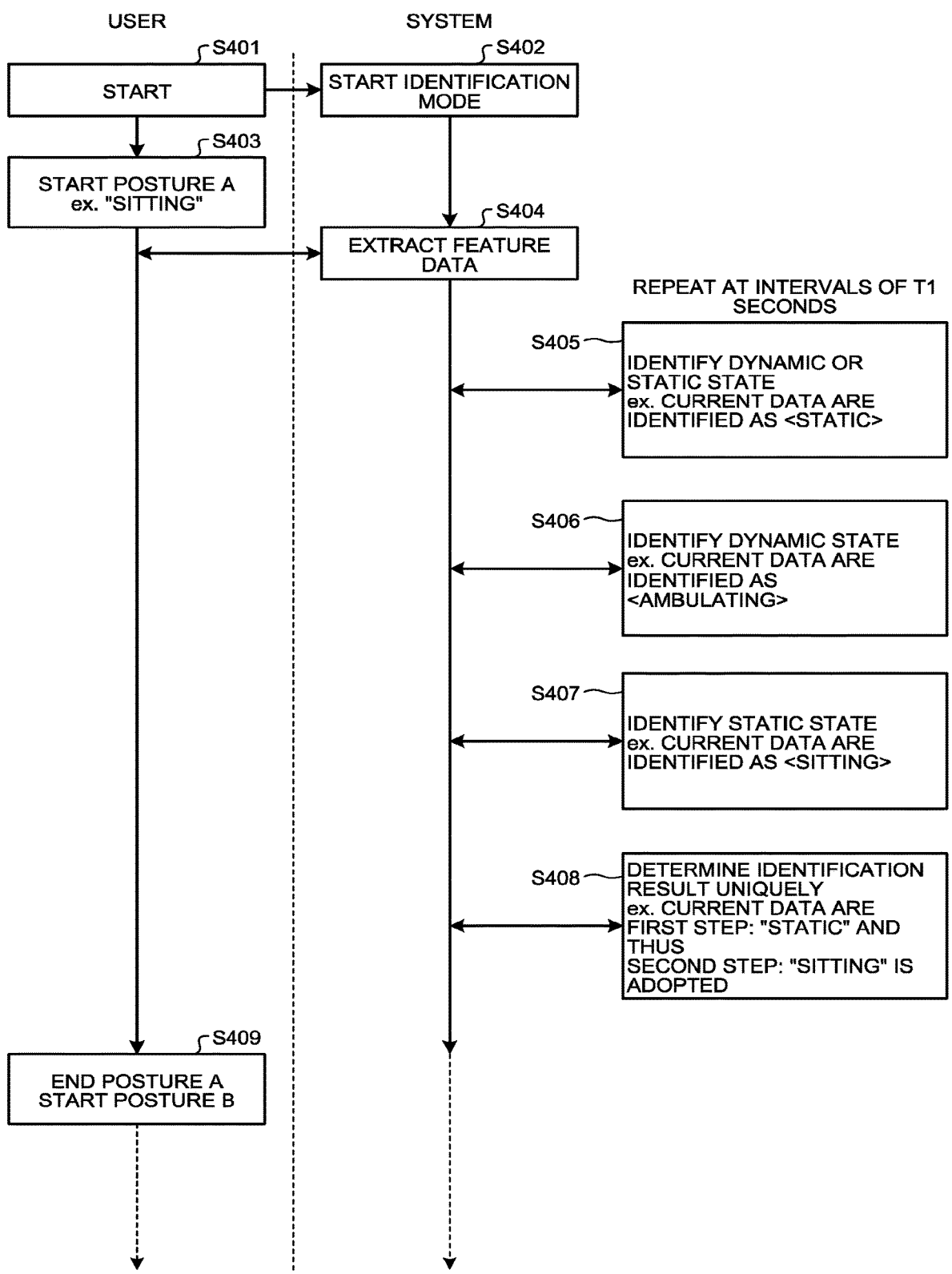

FIG.7

| | | POSTURE AFTER CHANGE | | |
| --- | --- | --- | --- | --- |
| | | RECUMBENT POSITION | SITTING POSITION | STANDING POSITION |
| POSTURE BEFORE CHANGE | RECUMBENT POSITION | | | |
| | HEART RATE IN-CREASE | PARASYMPATHETIC NERVE SYSTEM DOMINANCE RESPIRATORY PULSE INCREASE IN LF COMPONENT: ACTIVATION OF SYMPATHETIC NERVE SYSTEM <br> NO CHANGE IN POSTURE | ACTIVATION OF SYMPATHETIC NERVE SYSTEM | ACTIVATION OF SYMPATHETIC NERVE SYSTEM |
| | HEART RATE DE-CREASE | INCREASE IN HF COMPONENT: ACTIVATION OF PARASYMPATHETIC NERVE SYSTEM | DECREASE IN VENOUS RETURN VOLUME TRANSITIONAL ACTIVATION OF PARASYMPATHETIC NERVE SYSTEM | DECREASE IN VENOUS RETURN VOLUME TRANSITIONAL ACTIVATION OF PARASYMPATHETIC NERVE SYSTEM |
| | SITTING POSITION | | | |
| | HEART RATE IN-CREASE | INCREASE IN VENOUS RETURN VOLUME TRANSITIONAL ACTIVATION OF SYMPATHETIC NERVE SYSTEM | RESPIRATORY PULSE INCREASE IN LF COMPONENT: ACTIVATION OF SYMPATHETIC NERVE SYSTEM <br> NO CHANGE IN POSTURE | ACTIVATION OF SYMPATHETIC NERVE SYSTEM |
| | HEART RATE DE-CREASE | ACTIVATION OF PARASYMPATHETIC NERVE SYSTEM INCREASE IN HF COMPONENT SUPPRESSION OF SYMPATHETIC NERVE SYSTEM | INCREASE IN HF COMPONENT: ACTIVATION OF PARASYMPATHETIC NERVE SYSTEM | DECREASE IN VENOUS RETURN VOLUME TRANSITIONAL ACTIVATION OF PARASYMPATHETIC NERVE SYSTEM |
| | STANDING POSITION | | | |
| | HEART RATE IN-CREASE | INCREASE IN VENOUS RETURN VOLUME TRANSITIONAL ACTIVATION OF SYMPATHETIC NERVE SYSTEM | INCREASE IN VENOUS RETURN VOLUME TRANSITIONAL ACTIVATION OF SYMPATHETIC NERVE SYSTEM | SYMPATHETIC NERVE SYSTEM DOMINANCE INCREASE IN LF COMPONENT: ACTIVATION OF SYMPATHETIC NERVE SYSTEM <br> NO CHANGE IN POSTURE |
| | HEART RATE DE-CREASE | ACTIVATION OF PARASYMPATHETIC NERVE SYSTEM INCREASE IN HF COMPONENT SUPPRESSION OF SYMPATHETIC NERVE SYSTEM | PARASYMPATHETIC NERVE ACTIVITY AND SUPPRESSION OF SYMPATHETIC NERVE SYSTEM | INCREASE IN HF COMPONENT: ACTIVATION OF PARASYMPATHETIC NERVE SYSTEM |

FIG.9
(1)
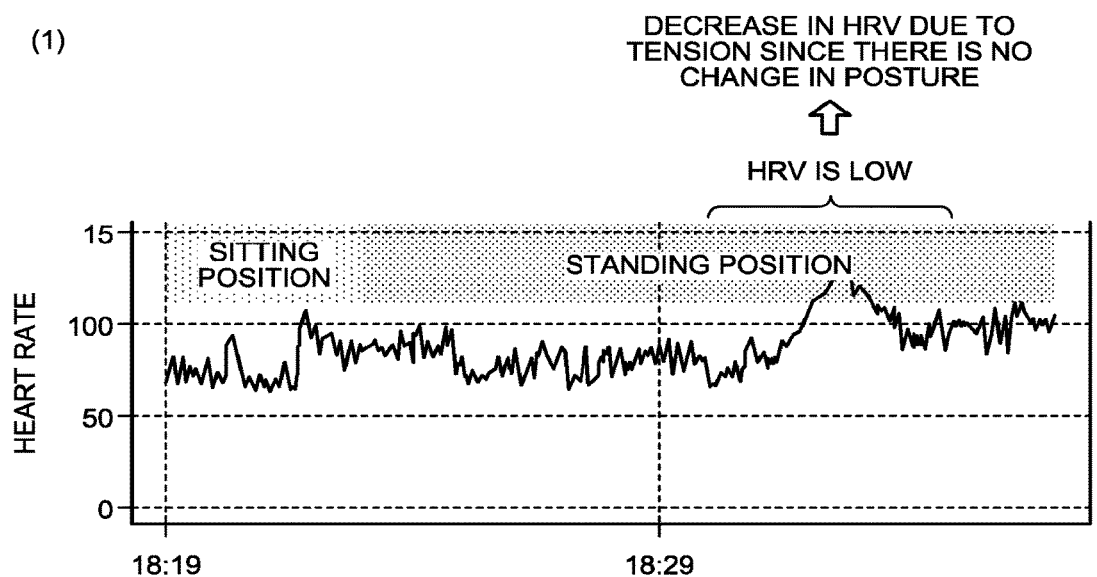
(2)
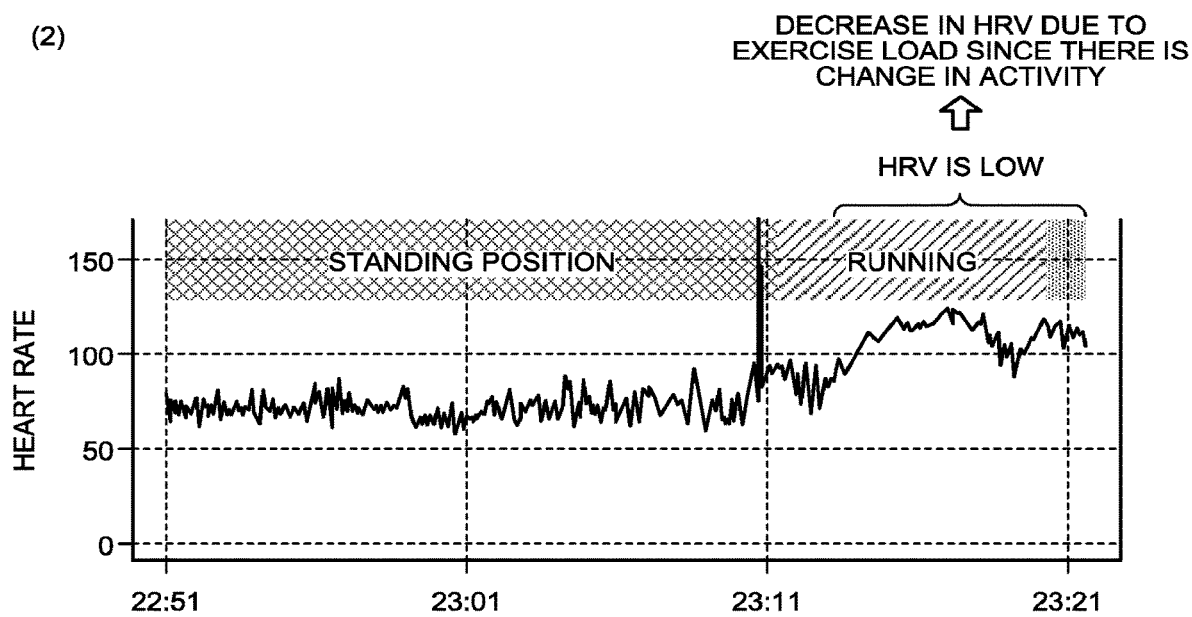

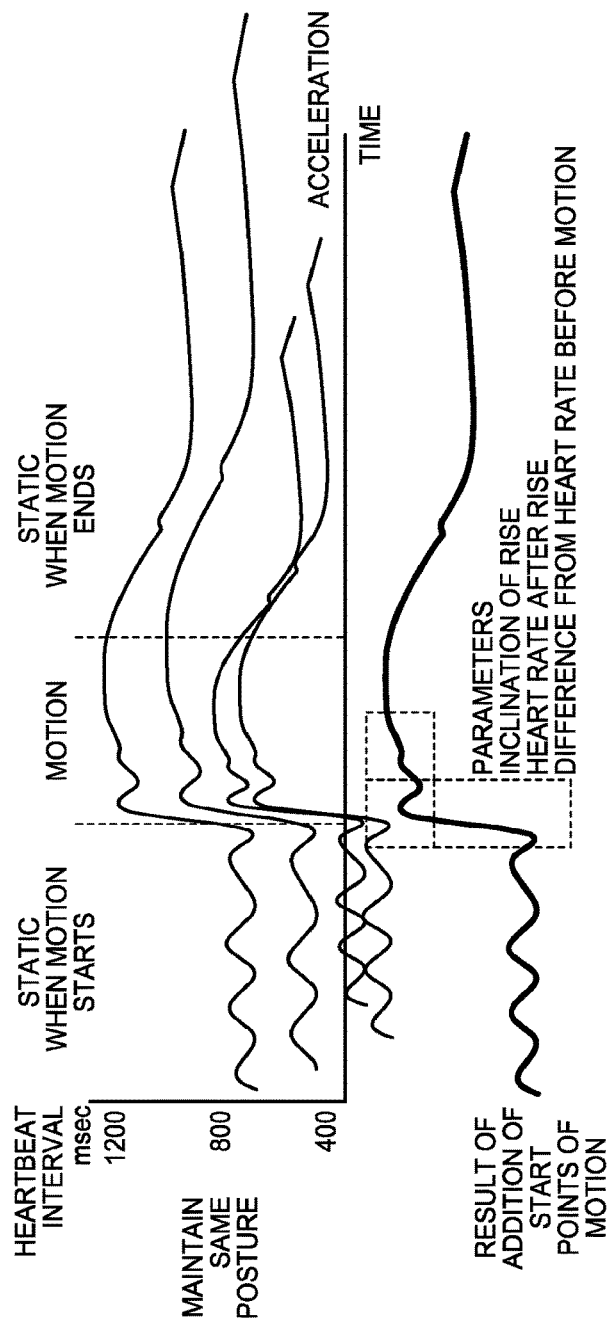
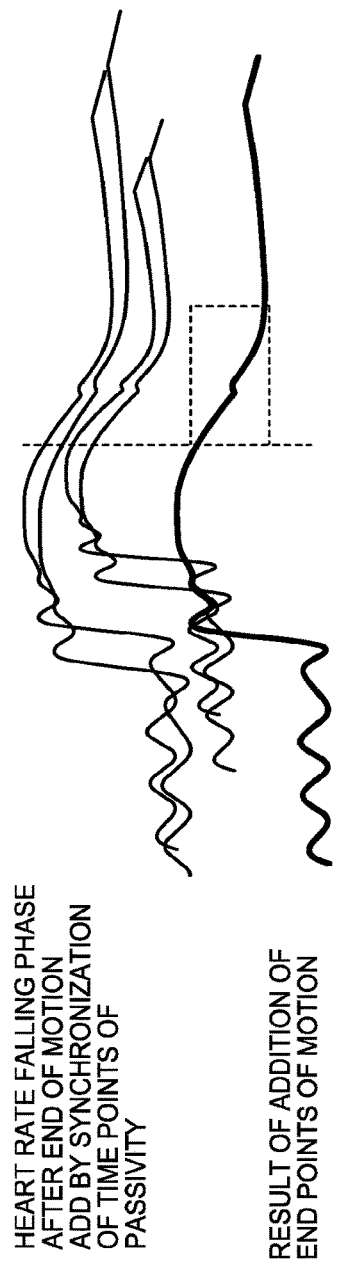
FIG.20

DEVICE AND METHOD FOR SEQUENTIAL POSTURE IDENTIFICATION AND AUTONOMIC FUNCTION INFORMATION ACQUISITION

FIELD

The present invention relates to a device, method, and program for sequential posture identification and autonomic function information acquisition.

BACKGROUND

In recent years, utilization of so-called wearable devices, i.e., information processing terminals which can be attached to human bodies (hereinafter, wearable devices) has expanded. Because it can be worn and carried by a user on a daily basis, a wearable device can be utilized in continuous and long-term monitoring of health conditions and lifestyle habits of the user. Further, technology for collecting, on a large scale, information related to users' health conditions and lifestyle habits collected by wearable devices is being popularized. Examples of such information on user's health conditions and lifestyle habits collectable by utilization of a wearable device include times of the user's sleep, exercise, work, commuting, meals, and the like.

Along with aging of society, countermeasures for increase of chronic diseases, such as high blood pressure and diabetes, and dealing promptly with heart attacks and cerebrovascular diseases (apoplexy) have become social challenges. Since these diseases are closely related to lifestyle habits, such as exercise and diet, there is a demand for prevention of these diseases and prevention of increase of these diseases by appropriate health management according to individual lifestyle habits.

Action estimation technology may be utilized for lifestyle habits, action patterns, and the like of an individual to be perceived. For example, according to an action estimation technique described in Non-Patent Literature 1, a single triaxial acceleration sensor is attached to a subject and acceleration data are acquired. Based on the acquired acceleration data, types of activity of the subject are estimated.

CITATION LIST

Non-Patent Literature

Non-Patent Literature 1: Akimitsu Akahori, Yoshifumi Kishimoto, and Koji Oguri, "A study of estimation of actions using a three-axis acceleration sensor", IEICE Technical Report, MBE, ME and Bio Cybernetics, The Institute of Electronics, Information and Communication Engineers, Dec. 2, 2005, Vol. 105, No. 456, pp. 49 to 52

SUMMARY

Technical Problem

However, when action estimation for a subject is performed by the conventional technique, in-depth estimation of posture and states of activity is difficult. For example, when an acceleration sensor is attached to the arm, movement of the torso and movement of the arm are not necessarily the same, and thus the posture of the subject may not be detected accurately. Further, just performing action estimation of a subject by use of an acceleration sensor may not directly lead to health management and disease prevention for the subject.

Embodiments disclosed herein have been made in view of the above, and aim to provide a technique for detecting a posture and a state of activity of a subject and enabling health management and disease prevention.

Solution to Problem

Sequential posture identification device, method, and program disclosed herein receive respectively, from an acceleration information measurement unit and a biological signal information measurement unit that are provided in a wearable device, acceleration information on motion of a subject whom the wearable device is attached to, and biological signal information of the subject. Further, the sequential posture identification device, method, and program extract, from the acceleration information and the biological signal information, first feature data corresponding to a first predetermined period and second feature data corresponding to a second predetermined period. Further, the sequential posture identification device, method, and program generate, by machine learning based on the first feature data, a dynamic/static activity identification model for identification of whether the subject is involved in a dynamic activity or in a static activity. The sequential posture identification device, method, and program generate, by machine learning based on the first feature data, a dynamic-activity identification model for identification of plural dynamic-activity patterns. The sequential posture identification device, method, and program generate, by machine learning based on the first feature data, a static-activity identification model for identification of plural static-activity patterns. The sequential posture identification device, method, and program determine, based on the dynamic/static activity identification model and the second feature data, whether the subject is involved in a dynamic activity or in a static activity in the second predetermined period. The sequential posture identification device, method, and program determine, based on the dynamic-activity identification model and the second feature data, a dynamic-activity pattern of the subject in the second predetermined period. The sequential posture identification device, method, and program determine, based on the static-activity identification model and the second feature data, a static-activity pattern of the subject in the second predetermined period. The sequential posture identification device, method, and program identify a posture and an activity of the subject in the second predetermined period, by combining results of the determination by first, second, and third determination units. The sequential posture identification device, method, and program generate correspondence information associating between the posture and the activity identified by an identification unit and biological signal information of the subject in the second predetermined period.

Further, autonomic function information acquisition device, method, and program disclosed herein receive respectively, from an acceleration information measurement unit and a biological signal information measurement unit that are provided in a wearable device, acceleration information on motion of a subject whom the wearable device is attached to, and biological signal information of the subject. By executing sequential machine learning for acceleration information and biological signal information in a first predetermined period, the autonomic function information acquisition device, method, and program identify a posture and an activity of the subject in a second predetermined period. The autonomic function information acquisition device, method, and program extract biological signal information corresponding to a combination of the same posture and activity that have been identified. The autonomic function information acquisition device, method, and program calculate a parameter of autonomic function evaluation, from the extracted biological signal information corresponding to the combination of the same posture and activity.

Advantageous Effects of Invention

The disclosed sequential posture identification device, sequential posture identification method, sequential posture identification program, autonomic function information acquisition device, autonomic function information acquisition method, and autonomic function information acquisition program achieve an effect of detecting a posture and a state of activity of a subject and enabling health management and disease prevention.

BRIEF DESCRIPTION OF DRAWINGS

FIG. 3 is a graph illustrating an example of measured values of triaxial acceleration and resultant acceleration detected by an acceleration sensor while a subject is ambulating.

FIG. 5 is a schematic diagram illustrating an example of a flow of a learning process in the sequential posture identification process by a sequential posture identification device according to the first embodiment.

FIG. 6 is a schematic diagram illustrating an example of a flow of an identification process (posture determination process) in the sequential posture identification process by the sequential posture identification device according to the first embodiment.

FIG. 7 is a table schematically illustrating correspondence between changes in posture of a subject and autonomic function evaluation.

FIG. 9 is a diagram for explanation of a case where similar changes occur in biological signal information for different postures and states of activity.

FIG. 20 is a diagram for explanation of a method of synchronously adding data for the transitional reaction of the heartbeat after the blood pressure increase due to the physical activity (exercise) of the subject, in the second embodiment.

DESCRIPTION OF EMBODIMENTS

Figure 1:
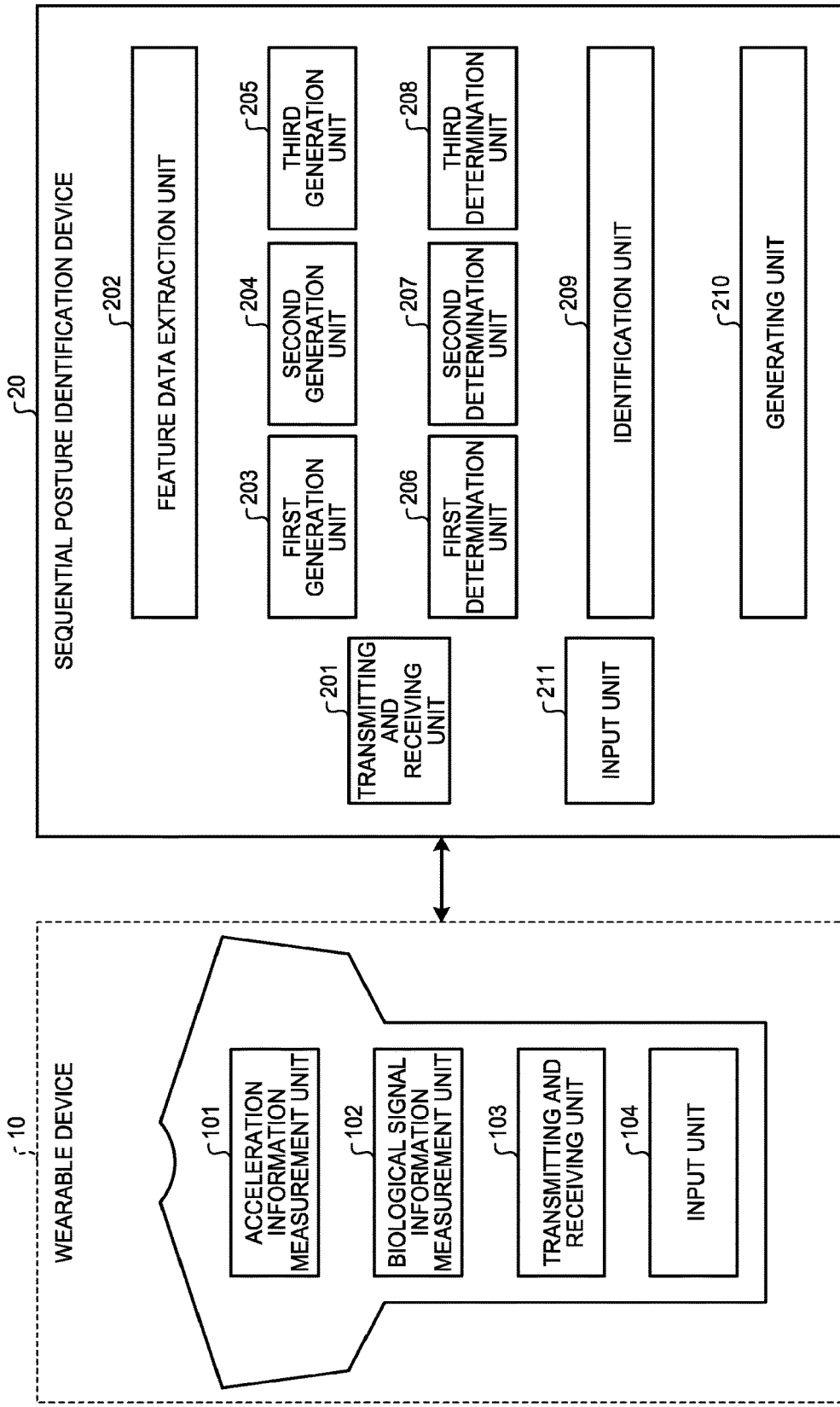
FIG. 1 is a schematic diagram illustrating an example of a configuration of a sequential posture identification system according to a first embodiment.

Hereinafter, embodiments of sequential posture identification device, method, and program, and autonomic function information acquisition device, method, and program disclosed herein will be described in detail, based on the drawings. This invention is not limited by these embodiments. Further, the embodiments may be combined with each other, as appropriate.

First of all, before description of the embodiments, significance of and problems in posture identification, and significance of and problems in autonomic function evaluation associated with posture identification will be described.

(Significance of and Problems in Posture Identification)

With the coming of a super aging society, research and study for enabling individuals to maintain their health, prevent diseases, and live independently are underway. Of such research and study, in-depth and long-term study related to a causal relation between lifestyle habits and diseases of individuals, in particular, study of information related to physical activity, posture, and exercise, is considered to be important.

Study of lifestyle habits has so far been implemented by a method, in which subjects themselves write answers to questions in questionnaires or the like, or by measurement using physical activity meters. However, in the self-assessment method, contents of the answers can be ambiguous and their accuracy is not stable. Further, even if actions or exercises of individuals in their lives are of the same type, depending on postures and action patterns of the individuals in those actions or exercises, loads actually exerted on their bodies and circulatory dynamics are different among the individuals.

Thus, there is a demand for a technique that enables posture and activity of a subject in the subject's daily life to be accurately perceived.

In addition, a load exerted on a body also depends on the individual's age and sex, cardiopulmonary function, presence of any disease, and the like. Therefore, by measuring, together with information related to the posture and activity, a biological signal such as a heart rate, the load exerted on the body is expected to be more accurately evaluated.

(Significance of and Problems in Evaluation of Autonomic Function)

Next, as to cardiocirculatory diseases, for which countermeasures are particularly in urgent need in aging societies, correlativity between autonomic functions of cardiocirculatory systems and death rates of cardiac patients has been noted thus far. Moreover, functional disorders, such as abnormality in the autonomic nervous system and deterioration of the regulatory function, have been considered to be related to development of cardiocirculatory diseases. Therefore, monitoring and evaluation of the autonomic function are considered to be important in prevention and reduction of cardiocirculatory diseases.

In an autonomic nerve examination implemented in hospitals and the like at present, for example, in a head-up tilt test, after fixing a subject on an examining table in a face-up position, the autonomic function is examined by passive change of the inclination angle of the examining table and measurement of the blood pressure, heart rate, and the like. The subject is fixed to be examined because posture of the body influences the autonomic function. However, a technique for enabling both detection of a change in the posture and examination of the autonomic function, while the subject leads his/her daily life, has not been proposed thus far.

Furthermore, as a method of measuring the heart rate variability and evaluating the autonomic function, there is a method of separately extracting a part where the heart rate accelerates (increasing phase) and a part where the heart rate decelerates (decelerating phase), and selectively quantifying each of these phases. In particular, the index quantifying only the decelerating phase is considered to be a predictor of the risk of death of a post-myocardial infarction patient, as an index indicating the parasympathetic nerve activity.

However, in the method of extracting a decelerating phase thus far, all decelerating phases have been uniformly quantified. That is, both a respiratory arrhythmia caused without a change in posture, and an autonomic reflex caused by a change in posture are similarly quantified as decelerating phases. That is, the quantified data include data with different causes and qualities, and have not led to a precise autonomic function evaluation.

First Embodiment

Based on the above, sequential posture identification device, method, and program, and autonomic function information acquisition device, method, and program, according to a first embodiment, will now be described.

In a sequential posture identification process according to the first embodiment, by measuring acceleration information and biological signal information from a subject and performing sequential machine learning by using both the acceleration information and the biological signal information, an identification model for identifying postures of the subject is generated. Further, in the sequential posture identification process according to the first embodiment, postures and states of activity of the subject are classified into two patterns, "dynamic and static", by use of the generated identification model, and what kinds of "dynamic" activity and what kinds of "static" activity the postures and states of activity correspond to are identified. Furthermore, in the sequential posture identification process according to the first embodiment, an identification process, in which a posture and an activity of the subject are identified, is executed in parallel with a learning process, by use of sequential machine learning. Moreover, in the sequential posture identification process according to the first embodiment, information indicating health status of the subject is generated by association between the identified posture and activity and the biological signal information measured from the subject.

Accordingly, in the first embodiment, by the identification of the posture and activity of the subject in consideration of both the acceleration information and the biological signal information, accurate identification of the posture and activity can be realized. Further, in the first embodiment, postures and activities of the subject are classified into plural "dynamic-activity" patterns and plural "static-activity" patterns, in addition to the classification into the two patterns, "dynamic and static", posture determination and activity determination based on plural identification models are executed in parallel with each other, and results of the determination are combined together. Therefore, the sequential posture identification process according to the first embodiment realizes identification of a posture and an activity based on fine classification executed in a short time. In addition, by utilization of the sequential machine learning, in contrast to a process, in which data for learning are prepared in advance and learning is performed at once, learning can be executed sequentially and results of the learning can be updated. Therefore, even if a base line of data changes due to a basic change in health status, posture, or the like of a subject, the posture identification process can be executed while learning is continuously performed. Further, by association between the biological signal information and the results of posture identification, information associating between the heart rate variability and posture changes, for example, may be generated, and more accurate evaluation of the health status of the subject may be realized.

(Example of Configuration of Sequential Posture Identification System According to First Embodiment)

FIG. 1 is a schematic diagram illustrating an example of a configuration of a sequential posture identification system 1 according to the first embodiment. The sequential posture identification system 1 illustrated in FIG. 1 includes a wearable device 10, and a sequential posture identification device 20. The wearable device 10 and the sequential posture identification device 20 are communicatably connected to each other via a network.

The type of the network connecting between the wearable device 10 and the sequential posture identification device 20 is not particularly limited, and the network may be a wired network, or a wireless network. However, in order to avoid obstruction of action of a subject whom the wearable device 10 is attached to; for the wireless network, preferably, for example, a smartphone or the like connected by Bluetooth (registered trademark) is utilized, or Wi-Fi or the like is utilized.

(Example of Configuration of Wearable Device 10)

The wearable device 10 is an electronic device that can be attached to and carried by the subject. In order to make it possible to measure movement of the trunk of the subject, the wearable device 10 is preferably shaped such that at least a part of the wearable device 10 is placed near the trunk of the subject. Specifically, the wearable device 10 is preferably shaped such that when the wearable device 10 is attached to the subject, the movement of the trunk of the subject may be detected by a measurement unit, such as a sensor included in the wearable device 10.

In the example of FIG. 1, the wearable device 10 has a shirt shape that is able to be put on and taken off by the subject. However, the shape of the wearable device 10 is not limited to be that of a shirt, and may be any shape, for example, a belt shape, as long as the wearable device 10 can be attached to the trunk of the subject. Further, a wearable computer including a processor and a memory may be used as the wearable device 10, and the wearable device 10 may be configured to store measured information in the wearable device 10, as appropriate.

The wearable device 10 includes an acceleration information measurement unit 101, a biological signal information measurement unit 102, a transmitting and receiving unit 103, and an input unit 104.

The acceleration information measurement unit 101 is a sensing device that detects and measures movement of the body of the subject. The acceleration information measurement unit 101 measures acceleration information of the body of the subject. For example, the acceleration information measurement unit 101 is formed of an acceleration sensor, for example, a triaxial acceleration sensor, which is placed near the trunk of the subject. The acceleration information measurement unit 101 measures acceleration of the movement of the body of the subject along three axes, the anteroposterior axis, the lateral axis, and the vertical axis. Hereinafter, "anteroposterior", "lateral", or "vertical" will be referred to based on a direction in which the body of the subject is directed when the wearable device 10 is attached to the subject and the subject is standing.

The acceleration information measurement unit 101 is arranged in the wearable device 10, such that when the wearable device 10 is attached to the subject, the acceleration information measurement unit 101 is placed near the trunk of the subject. In particular, the acceleration information measurement unit 101 is preferably arranged such that when the wearable device 10 is attached to the subject, the acceleration information measurement unit 101 is positioned at the chest of the subject. By such arrangement of the acceleration information measurement unit 101, acceleration information accurately reflecting the movement of the trunk of the subject may be acquired.

The biological signal information measurement unit 102 measures biological signal information that can be acquired from the body of the subject. The biological signal information measurement unit 102 is, for example, a sensing device that measures cardiac potential. The biological signal information measurement unit 102 measures, for example, information related to the cardiac potential and heartbeat of the subject. Specifically, the biological signal information measurement unit 102 measures the cardiac potential by single induction at regular intervals. Further, the biological signal information measurement unit 102 measures, for example, heartbeat intervals, that is, RR intervals. In addition, a pulse wave, such as a photoelectric pulse wave; body impedance, such as bioelectric resistance; biological microvibration or biopressure variation; arterial pressure, such as cuff pressure of a sphygmomanometer or the like; or the like, may be measured as a biological signal. Further, in addition, bioelectric potential, myoelectricity, electroencephalography, evoked potential, or the like, may be used.

The transmitting and receiving unit 103 transmits the acceleration information and biological signal information measured by the acceleration information measurement unit 101 and the biological signal information measurement unit 102, to outside of the wearable device 10. Further, the transmitting and receiving unit 103 receives a signal transmitted from the outside of the wearable device 10. Every time the acceleration information measurement unit 101 and the biological signal information measurement unit 102 acquire information, the transmitting and receiving unit 103 transmits the information to outside. For example, the transmitting and receiving unit 103 transmits information by a wireless communication function. Specifically, the transmitting and receiving unit 103 transmits the acceleration information and the biological signal information, to the sequential posture identification device 20.

The input unit 104 receives information that the subject or the like inputs into the wearable device 10. For example, the input unit 104 receives a label (described later) that the subject or the like inputs. The received label is sent to the transmitting and receiving unit 103 and transmitted to the sequential posture identification device 20. Based on a predetermined procedure, the sequential posture identification device 20 associates the label with the acceleration information and the biological signal information that are received after the label. Details of the label will be described later. Further, the label may be input from an input unit 211 (described later) included in the sequential posture identification device 20, instead of from the input unit 104. Furthermore, the wearable device 10 may be configured without the input unit 104. Moreover, the input unit 104 may be used for the subject or the like to select a learning mode or an identification mode, which will be described later.

(Example of Configuration of Sequential Posture Identification Device 20)

The sequential posture identification device 20 includes a transmitting and receiving unit 201, a feature data extraction unit 202, a first generation unit 203, a second generation unit 204, a third generation unit 205, a first determination unit 206, a second determination unit 207, a third determination unit 208, an identification unit 209, a generating unit 210, and the input unit 211.

The transmitting and receiving unit 201 receives the acceleration information and the biological signal information transmitted from the transmitting and receiving unit 103 of the wearable device 10. The transmitting and receiving unit 201 receives the acceleration information and the biological signal information sequentially transmitted by the transmitting and receiving unit 103, and sends the acceleration information and the biological signal information to the feature data extraction unit 202.

The feature data extraction unit 202 extracts feature data to be used in posture identification, from the acceleration information and the biological signal information. The extracted feature data are sent to the first generation unit 203, the second generation unit 204, and the third generation unit 205, and are used in a learning process, in which baseline information of postures and activities of the subject is acquired. The extracted feature data are further sent to the first determination unit 206, the second determination unit 207, and the third determination unit 208, and are used in an identification process, in which a posture and an activity of the subject are identified. Details of a feature data extraction process executed by the feature data extraction unit 202 will be described later. The feature data extraction unit 202 may be not an independent component, and processing of the feature data extraction unit 202 may be incorporated into each of the first generation unit 203, the second generation unit 204, the third generation unit 205, the first determination unit 206, the second determination unit 207, and the third determination unit 208.

The first generation unit 203, the second generation unit 204, and the third generation unit 205 execute a learning process, in which sequential machine learning is performed by use of the feature data. The first generation unit 203 generates a dynamic/static activity identification model for identification of a dynamic state and a static state of the subject. The second generation unit 204 generates a dynamic-activity identification model for identification of a type of activity when the subject is in the dynamic state. The third generation unit 205 generates a static-activity identification model for identification of a type of activity when the subject is in the static state. The dynamic/static activity identification model, the dynamic-activity identification model, and the static-activity identification model generated by the learning process serve as the baseline information of postures and activities of the subject. The learning process is a process, in which these identification models are generated, that is, a process, in which the baseline information is acquired. Details of the learning process will be described later.

The first determination unit 206, the second determination unit 207, and the third determination unit 208 identify a posture and an activity of the subject by respectively using the identification models generated by the first generation unit 203, the second generation unit 204, and the third generation unit 205, and the feature data extracted by the feature data extraction unit 202.

By using the dynamic/static activity identification model generated by the first generation unit 203, the first determination unit 206 determines whether the subject is in the dynamic state or the static state. By using the dynamic-activity identification model generated by the second generation unit 204, the second determination unit 207 determines a type of dynamic activity indicating what kind of activity the subject is performing when the subject is in the dynamic state. By using the static-activity identification model generated by the third generation unit 205, the third determination unit 208 determines a type of static activity indicating a kind of activity when the subject is performing when the subject is in the static state. Details of a posture determination process by the first determination unit 206, the second determination unit 207, and the third determination unit 208 will be described later.

The identification unit 209 identifies a posture and an activity of the subject by combining together results of the posture determination process by the first determination unit 206, the second determination unit 207, and the third determination unit 208. As a result of the identification process by the identification unit 209, an identification result for the posture and activity of the subject is acquired. For example, an identification result indicating that the subject is "dynamic", and is "ambulating" is acquired. Details of the identification process will also be described later.

The generating unit 210 generates information chronologically associating between the identification result of the identification unit 209 and the biological signal information received from the wearable device 10.

The generating unit 210 generates correspondence information associating a posture and an activity of the subject identified based on acceleration information and biological signal information acquired in a predetermined period, with the biological signal information acquired in the same period. For example, the generating unit 210 generates correspondence information by associating a posture and an activity of a subject from a time T1 to a time T5 with the heart rate of the subject from the time T1 to the time T5. Details of the information generated by the generating unit 210 will also be described later.

The input unit 211 receives input of information from outside of the sequential posture identification device 20. The input unit 211 may be, for example, an input device, such as a keyboard or a touch pad. Similarly to the input unit 104 of the wearable device 10, the input unit 211 may be used by a subject or the like in inputting a label, which will be described later. Further, the input unit 211 may be used for a subject or the like to select the learning mode or the identification mode.

(Example of General Flow of Sequential Posture Identification Process)

Figure 2:
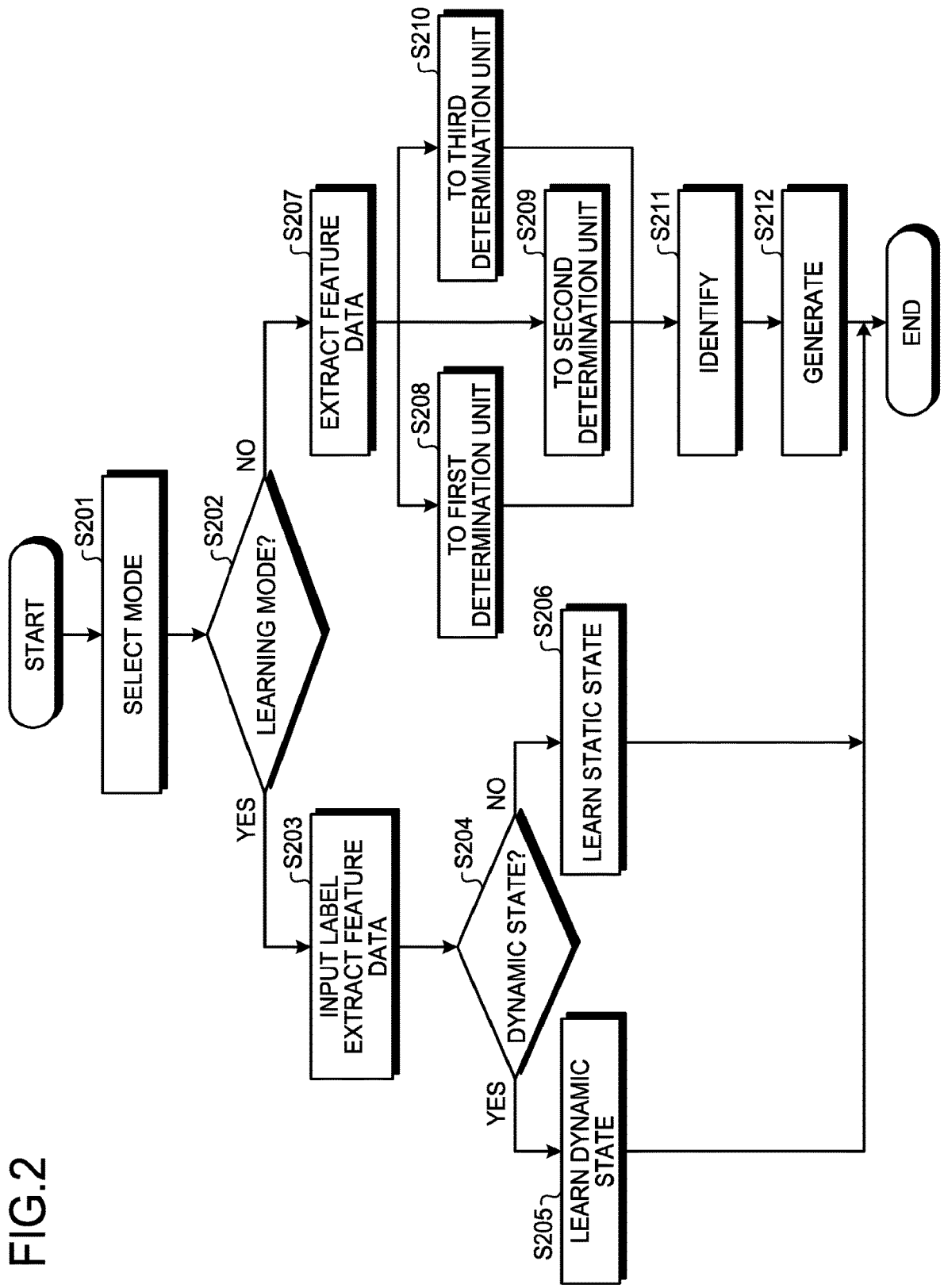
FIG. 2 is a flow chart illustrating an example of a flow of a sequential posture identification process according to the first embodiment.

FIG. 2 is a flow chart illustrating an example of a flow of the sequential posture identification process according to the first embodiment. When the process is started, the sequential posture identification device 20 receives selection of a mode (Step S201). Specifically, selection of the learning mode or the identification mode is received. The learning mode is an operation mode, in which the sequential posture identification device 20 executes the learning process. Further, the identification mode is an operation mode, in which the sequential posture identification device 20 executes the identification process (including the posture determination process). For convenience of explanation, FIG. 2 illustrates a configuration, in which either the learning mode or the identification mode is selected, but a mode, in which the learning process and the identification process are executed in parallel with each other, may be provided further and made to be executable.

Subsequently, the sequential posture identification device 20 determines whether or not the learning mode has been selected (Step S202). If the learning mode has been selected (Step S202; Yes), the sequential posture identification device 20 receives a label input by a subject or the like. The label is information specifying "posture" and "activity" of the subject. For example, the label includes information on "posture", such as "standing position", "sitting position", or "recumbent position", and information on "activity", such as "dynamic state" or "static state". Further, a label, such as "ambulating", "jumping", "stepping in place", or "walking", may be generated as "activity". "Ambulating" simply refers to common ambulating, and "walking" refers to initiative walking as exercise. The sequential posture identification device 20 is able to identify common "ambulating", and "walking" as exercise, by determining exercise intensities also for activities that are similar to each other as states of activity of the body. As described above, the sequential posture identification device 20 is able to give different labels respectively to activities that are similar to each other but have different intensities, and to identify the activities. Upon the learning process, since what kind of information on "posture and activity" is information to be learnt is caused to be stored in the sequential posture identification device 20, feature data and a label including information on the two "posture and activity" are processed in association with each other.

The sequential posture identification device 20 then extracts feature data from the acceleration information and the biological signal information received from the wearable device 10. The received label and the extracted feature data are input to the first generation unit 203, the second generation unit 204, and the third generation unit 205 (Step S203). Each of the generation units 203, 204, and 205 determines whether or not the label indicates "dynamic state" (Step S204). If it is determined that the label indicates "dynamic state" (Step S204; Yes), the first generation unit 203 executes machine learning based on the feature data, and generates or updates the dynamic/static activity identification model (Step S205). Further, the second generation unit 204 executes machine learning based on the feature data, and generates or updates the dynamic-activity identification model (Step S205). If it is determined that the label indicates "dynamic state" (Step S204; Yes), the third generation unit 205 does not execute machine learning.

If it is determined that the label indicates "static state" (Step S204; No), the first generation unit 203 executes machine learning based on the feature data, and generates or updates the dynamic/static activity identification model (Step S206). Further, the second generation unit 204 does not execute machine learning. The third generation unit 205 executes machine learning based on the feature data, and generates or updates the static-activity identification model (Step S206). The processing in the learning mode is then ended.

On the contrary, it will now be assumed that at Step S202, it is determined that the learning mode has not been selected, that is, that the identification mode has been selected (Step S202; No). In this case, the sequential posture identification device 20 extracts feature data from the acceleration information and the biological signal information received from the wearable device 10 (Step S207). The sequential posture identification device 20 then sends the feature data to the first determination unit 206, the second determination unit 207, and the third determination unit 208. The first determination unit 206 determines, based on the feature data and the dynamic/static activity identification model that has been generated already, whether the subject is in the dynamic state or the static state (Step S208). The second determination unit 207 determines, based on the feature data and the dynamic-activity identification model that has been generated already, what a kind of the dynamic state it is (Step S209). The third determination unit 208 determines, based on the feature data and the static-activity identification model that has been generated already, what a kind of the static state it is (Step S210).

Results of the determination by the first determination unit 206, the second determination unit 207, and the third determination unit 208 are sent to the identification unit 209, and based on the results of the determination, the identification unit 209 identifies a posture and an activity of the subject (Step S211). For example, the identification unit 209 identifies that a posture and an activity of the subject at that time point are "standing position and dynamic state". The sequential posture identification device 20 then generates information chronologically associating the identification result with the biological signal information corresponding to the identification result (Step S212). The identification process is then ended.

Next, each of the feature data extraction process, the learning process, and the identification process (including the posture determination process), which are included in the sequential posture identification process, will be described further.

(Example of Feature Data Extraction Process)

In the sequential posture identification device 20 of the first embodiment, the feature data extraction unit 202 receives, from the wearable device 10, acceleration information and biological signal information measured in a predetermined period, and divides the predetermined period into plural periods overlapping one another and having different lengths from one another. The feature data extraction unit 202 then calculates a set of feature data for each of these periods. These plural sets of feature data are used in the learning process and the posture determination process. Feature data and their extraction cycles (T1 to T4 described below) used by the first generation unit 203 are the same as feature data and their extraction cycles used by the first determination unit 206. Further, feature data and their extraction cycles used by the second generation unit 204 are the same as feature data and their extraction cycles used by the second determination unit 207. Furthermore, feature data and their extraction cycles used by the third generation unit 205 are the same as feature data and their extraction cycles used by the third determination unit 208. However, the feature data and their extraction cycles used by the first generation unit 203, the feature data and their extraction cycles used by the second generation unit 204, and the feature data and their extraction cycles used by the third generation unit 205 may be different from one another.

(First Feature Data)

As first feature data, the feature data extraction unit 202 calculates a fundamental statistic in a set of time series of acceleration information of each axis in T1 seconds. For example, at least one of a maximum value, a minimum value, an average value, and a variance value is calculated. For example, it will be assumed that T1=0.4 second, and ten pieces of acceleration information are measured for each axis in 0.4 second. In this case, the feature data extraction unit 202 extracts a fundamental statistic of ten pieces of information for each axis as feature data of that axis.

(Second Feature Data)

As second feature data, the feature data extraction unit 202 calculates a fundamental statistic in a set of time series of acceleration information of each axis in T2 seconds (where T1<T2). For example, at least one of a maximum value, a minimum value, an average value, and a variance value is calculated. For example, T2=2 seconds.

(Third Feature Data)

As third feature data, the feature data extraction unit 202 calculates at least one of: a vibration frequency along each axis in T3 seconds (where T2<T3); an average value or a variance value of overall vibration frequencies; and an average value or a variance value of heart beat intervals extracted from the biological signal information. The vibration frequency is feature data corresponding to the number of vibrations of the body of the subject. A method of detecting the vibration frequency will be described in detail below.

(Fourth Feature Data)

As fourth feature data, the feature data extraction unit 202 calculates at least one of: a vibration frequency along each axis in T4 seconds (where T3<T4); a fundamental statistic of overall vibration frequencies; or a fundamental statistic of heart beat intervals extracted from the biological signal information. Examples of the fundamental statistic include a maximum value, a minimum value, an average value, and a variance value.

The feature data calculated from the heart beat intervals are not limited to the average value or the variance value of the heart beat intervals. For example, a fundamental statistic of heart rates may be calculated as feature data. Further, not all of the above described feature data may be used as the first, second, third, and fourth feature data, and depending on the posture and activity to be identified, only some of the feature data are used.

(Method of Detecting Vibration Frequency)

Next, the method of detecting the vibration frequency will be described. "The vibration frequency" is a frequency having the same meaning as the number of vibrations of a body, such as the number of steps or the number of jumps, with respect to a vertical direction of the body. By use of the vibration frequency as feature data for posture identification, an identification model in consideration of the degree of inclination and the vibration, that is, shaking, of the body of a subject is able to be generated and detailed identification of posture and activity can be realized.

When the vibration frequency is used as feature data, the acceleration information measurement unit 101 includes, in order to measure the vibration of the body of the subject whom the wearable device 10 is attached to, at least the acceleration sensor, such as the triaxial acceleration sensor. If the triaxial acceleration sensor is used, for example, acceleration received by the acceleration sensor along the three axes, an X-axis, a Y-axis, and a Z-axis (see FIG. 3) can be measured.

FIG. 3 is a diagram for explanation of the method of detecting the vibration frequency, of the feature data to be used in the sequential posture identification process. When a subject changes posture or moves and the acceleration sensor is inclined, gravitational acceleration detected by the acceleration sensor is changed. Thereby, inclination of the acceleration sensor, that is, the inclination of the body of the subject, can be detected. Further, by change in resultant acceleration of acceleration along the respective X, Y, and Z-axes detected by the acceleration sensor, the degree of vibration of the acceleration sensor, that is, of the body of the subject, can be detected. For example, FIG. 3 is a graph illustrating an example of measured values of triaxial acceleration and resultant acceleration detected by an acceleration sensor while a subject is walking.

The vibration frequency is detected by use of the measured values acquired by the acceleration sensor, as described above. Hereinafter, an example of the method of detecting the vibration frequency will be described.

Firstly, resultant acceleration $A_r$ is calculated based on the following Equation (1).

$$A_r = \sqrt{A_x^2 + A_y^2 + A_z^2} \quad (1)$$

Figure 4:
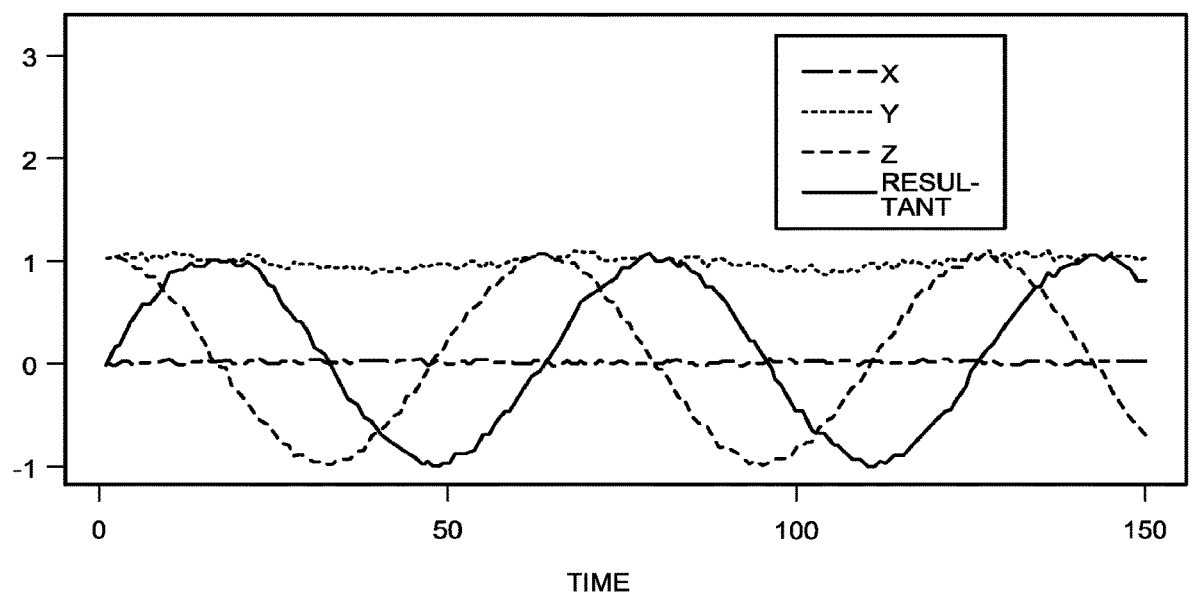
FIG. 4 is a graph illustrating an example of the acceleration and resultant acceleration when the sensor is rotated.

With the resultant acceleration $A_r$ defined by Equation (1), vibration with respect to the respective axial directions can be detected equally, and if there is movement, such as rotation, of the sensor, the resultant acceleration is substantially unchanged. FIG. 4 is a graph illustrating an example of the acceleration and resultant acceleration when the sensor is rotated. In the example of FIG. 4, rotational motion in the Z-axis direction is caused, but the resultant acceleration substantially follows measured values along the Z-axis.

Next, when the resultant acceleration $A_r$ is less than a predetermined lower limit threshold $\theta_{btm}$, the resultant acceleration $A_{btm}$ at that time is recorded. When the resultant acceleration $A_r$ exceeds a predetermined upper limit threshold $\theta_{top}$ within a predetermined upper limit time $t_w$ from the recording of the resultant acceleration $A_{btm}$ that is less than the lower limit threshold $\theta_{btm}$, the resultant acceleration $A_{top}$ at that time is recorded. By this processing, a period, in which the value of the resultant acceleration largely changes in a short time, is detected.

Next, whether or not a difference between the recorded $A_{btm}$ and $A_{top}$ is larger than a predetermined vibration detection threshold $\theta_{amp}$ is determined. If the difference is larger than the vibration detection threshold $\theta_{amp}$, the vibration frequency is counted as "1". The $A_{btm}$ and $A_{top}$ are then reset. Further, when there is no count for the vibration frequency within a predetermined upper limit period $t_w$, the $A_{btm}$ and $A_{top}$ are also reset.

By the above described process, when strong acceleration is being exerted in a certain direction for a long time, a count is not added to the vibration frequency, and a body vibration, in which the direction of acceleration suddenly changes, can be detected accurately.

Any method may be used, without any particular limitation, as the method of detecting the vibration frequency, as long as: (1) rotation or long term change is not detected as vibration; (2) when acceleration does not change by a certain amount, the change is not detected as vibration; (3) detection is possible in any axial direction with the same algorithm; and (4) detection is possible from acceleration, angular velocity information, or the like that is acquired. As described above, the vibration frequency is calculated, regardless of the motion specific to the resultant acceleration, for any direction without distinction between an anteroposterior direction and a lateral direction. The feature data extraction unit 202 according to the first embodiment divides T3 into a few small divided frames and calculates, based on a vibration frequency in each of these small frames, a variance value and an average value.

Further, "vibration frequency along each axis" is a number acquired as a result of counting, when a vibration frequency is detected, only for an axis that has influenced that vibration the most. For example, of components constituting resultant acceleration when a vibration frequency is counted by the above described method, an axis, along which the largest acceleration has been measured, is detected. A vibration frequency along this axis is then counted as "1". For example, if the largest acceleration of accelerations along the respective axes when the vibration frequency is counted as "1" has been detected from the Z-axis, the vibration frequency along the Z-axis is counted as "1". Vibration along the Z-axis is detected, for example, upon vibration when a subject is ambulating, or when the subject jumps. Therefore, based on the vibration frequency along the Z-axis, an activity, such as "ambulating", can be detected.

Since the sequential posture identification device 20 according to the first embodiment adopts a machine learning model, weighting of respective feature data is automatically performed.

(Example of Flow of Learning Process)

FIG. 5 is a schematic diagram illustrating an example of a flow of the learning process of the sequential posture identification process by the sequential posture identification device 20 according to the first embodiment. By use of FIG. 5, a specific example of the learning process will be described.

When machine learning is executed for the first time or when machine learning is additionally executed, in the sequential posture identification device 20, a user instructs the sequential posture identification device 20 to start execution of the learning process, by, for example, selecting the learning mode (Step S300). The user then performs registration of a posture. That is, the user inputs a label. In other words, the user inputs, to the sequential posture identification device 20: information identifying a motion to be machine learnt (a name of a posture A"); "posture" of the motion; and information on which of "dynamic state" and "static state" the motion corresponds to ("preparation for registration of posture A", Step S301). For example, in the example of FIG. 5, "sitting" is input as "name of posture A". Since the sitting state is "static state", information indicating a state of activity, "static", is also input. In the example of FIG. 5, the posture, "sitting", is identified thereby. When a state that is even more detailed is to be identified, the identification is dealt with by adjustment of classification of postures and states of activity indicated by labels. For example, correspondingly to the name, "sitting"; information, "posture: sitting position" and "state of activity: static", may be input. Further, correspondingly to the name, "jumping"; "posture: standing position", "state of activity: vertical jumping", and the like, may be input. The input may be performed through the input unit 104 of the wearable device 10, or may be performed through the input unit 211. A label is input for each of motions to be subjected to machine learning, and is caused to be acquired and stored by the sequential posture identification device 20 (Step S302).

After the input of the label, the user instructs the sequential posture identification device 20 to start machine learning of the motion corresponding to the input label ("start posture A, Step S303). The user then starts the motion corresponding to the input label. By the input of the instruction of the user, the learning mode is started in the sequential posture identification device 20 (Step S304). The feature data extraction unit 202 of the sequential posture identification device 20 then executes the feature data extraction process (Step S305). As described above, the feature data extraction process is repeated for each of predefined periods (T1 to T4) for respective feature data.

When feature data are extracted, the feature data are transmitted to the first generation unit 203, the second generation unit 204, and the third generation unit 205. Based on the input label (for example, "sitting: static"), the first generation unit 203 executes machine learning of the input feature data as data of "dynamic state" or "static state" specified by the label (for example, when the label is "sitting: static", "static state") (Step S306). In the example of FIG. 5, the machine learning is executed every T1 seconds, the time, in which the feature data are extracted. The feature data extracted in an extraction cycle shorter than T1 seconds are slidingly input. An execution cycle of the machine learning may be set according to measurement cycles of the acceleration information measurement unit 101 and the biological signal information measurement unit 102.

Similarly, the second generation unit 204 also executes processing, based on the input label (for example, "sitting: static"). In the example of FIG. 5, since the input label is "sitting: static", that is, "static state", the second generation unit 204, which is a component that generates an identification model for the dynamic state, waits without executing machine learning (Step S307).

Similarly, the third generation unit 205 also executes processing, based on the input label (for example, "sitting: static"). In the example of FIG. 5, since the input label is "sitting: static", that is, "static state", the third generation unit 205 executes machine learning of input feature data, as one type of "static state" (Step S308).

When the motion specified by the label is completed, the user instructs the sequential posture identification device 20 to end the machine learning for that motion ("end posture A", Step S309). In response to the user's instruction, the sequential posture identification device 20 terminates the learning mode (Step S310). The user then starts preparation for registration of a posture B to be subjected to machine learning next (Step S311). The above is the flow of an example of machine learning in the sequential posture identification process.

The labels to be used in the learning process indicate postures and states of activity of motions to be identified, and include, for example: "ambulating", "jumping", "sitting", "standing", "lying on the stomach", "lying on the back", and the like; and display of whether that corresponds to the dynamic state or the static state.

(Example of Flow of Identification Process)

FIG. 6 is a schematic diagram illustrating an example of a flow of the identification process (including the posture determination process) of the sequential posture identification process by the sequential posture identification device 20 according to the first embodiment. Next, while reference is made to FIG. 6, a specific example of the posture determination process and the identification process will be described. Even if the sequential posture identification device 20 according to the first embodiment is executing the posture determination process and the identification process illustrated in FIG. 6, the sequential posture identification device 20 is able to execute the learning process of FIG. 5 in parallel with the posture determination process and the identification process, and to update the identification models as appropriate.

When the identification process is started, a user firstly inputs an instruction to start the identification process to the sequential posture identification device 20 (Step S401). For example, the user inputs selection of the identification mode. In response to the user's input, the sequential posture identification device 20 starts the identification mode (Step S402). When the identification mode is started, feature data extracted by the feature data extraction unit 202 are input to the first determination unit 206, the second determination unit 207, and the third determination unit 208. Differently from the learning mode, the user immediately starts an arbitrary motion without inputting specification of a label ("start posture A", Step S403). For example, the user starts the motion, "sitting". The wearable device 10 attached to the user measures acceleration information and biological signal information of the user and transmits the acceleration information and biological signal information to the sequential posture identification device 20. Based on the received acceleration information and biological signal information, the sequential posture identification device 20 then extracts feature data (Step S404). The feature data extraction process is executed, as described above, for each predefined period for the respective feature data. The extracted feature data are input to the first determination unit 206, the second determination unit 207, and the third determination unit 208.

Based on the input feature data and the dynamic/static activity identification model already generated by the first generation unit 203, the first determination unit 206 determines to which of the dynamic state and the static state the current feature data correspond. In the example of FIG. 6, the first determination unit 206 determines that a state corresponding to the input feature data is "static state" (that is, "static") (Step S405).

Based on the input feature data and the dynamic-activity identification model already generated by the second generation unit 204, the second determination unit 207 determines that the current feature data correspond to "ambulating", of the dynamic state (Step S406).

Based on the input feature data and the static-activity identification model already generated by the third generation unit 205, the third determination unit 208 determines that the current feature data correspond to "sitting", of the static state (Step S407). In the example of FIG. 6, the posture determination process is repeatedly executed every T1 seconds.

When the posture determination process by the first determination unit 206, the second determination unit 207, and the third determination unit 208 is completed, the respective determination results are transmitted to the identification unit 209. The identification unit 209 combines the three determination results together and outputs a final identification result. Specifically, the identification unit 209 firstly refers to the determination result by the first determination unit 206 (first step, Step S408). Since the determination result by the first determination unit 206 is "static", that is, "static state"; the determination result, "sitting", of the third determination unit 208 that executes determination with the static-activity identification model is adopted (second step, Step S408), and the user is identified to be "static: sitting".

As described above, in the identification process, the identification unit 209 checks, in the first step, to which of "dynamic state" and "static state" the feature data correspond (the determination result of the first determination unit 206), and thereafter, according to a result of the first step, selects, in the second step, the determination result for "dynamic state" or "static state".

When the user proceeds to another motion, without any particular input to the sequential posture identification device 20, the user proceeds to the different motion ("end posture A and start posture B", Step S409). According to a change in motion of the user, the acceleration information and the biological signal information transmitted to the sequential posture identification device 20 are changed, and the feature data are thus changed. Thereby, the posture change is reflected in the result of the identification process (including the posture determination process) executed by the sequential posture identification device 20 for each T1.

(Example of Autonomic Function Evaluation)

As described above, the sequential posture identification device 20 according to the first embodiment identifies a posture and a state of activity of a subject. Further, the generating unit 210 of the sequential posture identification device 20 generates information that can be used in determination of health conditions of the subject, by associating the identified posture and state of activity with change in biological signal information. Next, as an example of the information generated by the generating unit 210, information associating between posture change and autonomic function will be described.

FIG. 7 is a table schematically illustrating correspondence between change in posture of a subject and autonomic function evaluation. In the example of FIG. 7, heart rate is used as an index for autonomic function evaluation. As indices for evaluation of the autonomic function from the heart rate variability, a high frequency variation component (HF component) corresponding to respiration variation and a low frequency variation component (LF component) corresponding to blood pressure variation are generally used. In the example of FIG. 7, states of the autonomic nerve are evaluated by use of the heart rate, the HF component, and the LF component.

For example, it will be supposed that when posture of a subject changes from "standing position" to "sitting position", the heart rate is reduced. In this case, it is considered that the parasympathetic nerve activity of the autonomic nerve has been activated. Further, it will be supposed that when posture of a subject changes from "standing position" to "sitting position", the heart rate is increased. In this case, it is considered that the sympathetic nerve activity of the autonomic nerve due to an increase in the venous return has been transitionally activated. Further, it can be similarly considered for a case where a subject changes from "sitting position" to "recumbent position", or a case where there is no change in posture and the subject is in the static state.

On the contrary, it will be supposed that when posture of a subject changes from "sitting position" to "standing position", the heart rate is reduced. In this case, it is considered that the parasympathetic nerve activity is in a transitional hyperactive state due to a change in the circulatory dynamics, such as a decrease in the venous return. Further, it will be supposed that when posture of a subject changes from "standing position" to "sitting position", the heart rate is increased. In this case, it is considered that the sympathetic nerve activity is in a transitional hyperactive state due to a change in the circulatory dynamics, such as an increase in the venous return. Further, it can be similarly considered for a case where a subject changes from "recumbent position" to "sitting position", or a case where the posture changes from "recumbent position" to "standing position".

If the heart rate varies in a period, which has no transition of the posture of the subject, or in a period, which is maintained in the static state or dynamic state without change, evaluation based on the HF component or LF/HF ratio is possible. For example, the state of activity of the parasympathetic nerve system can be evaluated based on the HF component. Further, the state of activity of the sympathetic nerve system can be evaluated based on the LF/HF ratio. Furthermore, the parasympathetic nerve activity component (reduction in the heart rate due to a respiratory pulse, or the like) can be identified based on a falling phase of the heart rate.

Similarly, in a period, which has no change in the posture or state, the sympathetic nerve activity can be evaluated from an increase in the LF/HF ratio or LF component, or a reduction in the HF component. Further, the sympathetic nerve activity can be identified based on a rising phase of the heart rate. The example of FIG. 7 illustrates the relation between the change in posture and the autonomic function evaluation, the relation having been simplified.

Figure 8:
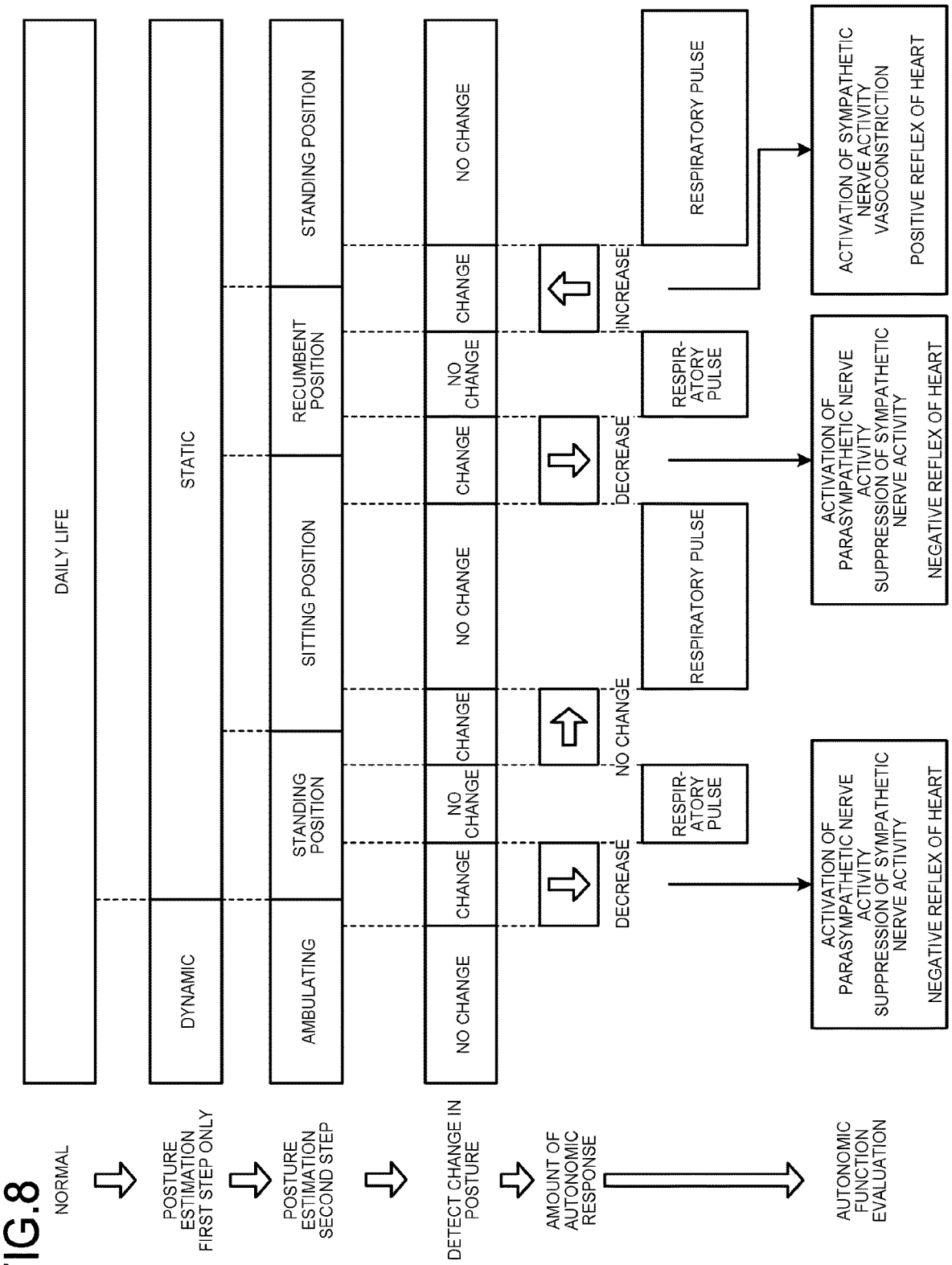
FIG. 8 is a diagram for explanation of a method of autonomic function evaluation in the sequential posture identification process according to the first embodiment.

Based on evaluation like that illustrated in FIG. 7, the generating unit 210 generates information on evaluation of the autonomic nerve by associating the change in posture with the amount of autonomic response. For example, FIG. 8 is a diagram for explanation of an example of a method of autonomic function evaluation. In the example illustrated in FIG. 8, firstly, the first determination unit 206 performs determination of which state of "dynamic or static" a subject is in, based on feature data ("posture estimation: first step only"). Subsequently, based on a result of the first step, the second determination unit 207 or the third determination unit 208 performs determination of what kind of dynamic state or static state the subject is in ("posture estimation: second step"). Thereby, states of "posture and activity" at each time point are identified. Next, the generating unit 210 determines, based on a result of the identification, a time point, at which the change in posture has occurred ("posture change detection"). The generating unit 210 then performs evaluation of the autonomic function ("autonomic function evaluation"), from the biological signal information corresponding to the determined time point, for example, information on the heart rate ("amount of autonomic response").

In the autonomic function evaluation illustrated in FIG. 7, the HF component and the LF component of frequency components of the heart rate variability (HRV) are feature data used in the autonomic function evaluation. However, not being limited thereto, in the autonomic function evaluation, other feature data may be used. For example, the variation amount of the heartbeat intervals may be used as feature data.

Effects of First Embodiment

As described above, a sequential posture identification device according to the first embodiment includes an acceleration information measurement unit that: is provided in a wearable device; and measures acceleration information of motion of a subject whom the wearable device is attached to. Further, the sequential posture identification device includes a biological signal information measurement unit that: is provided in the wearable device; and measures biological signal information of the subject. Furthermore, the sequential posture identification device includes a feature data extraction unit that extracts, from the acceleration information and the biological signal information, first feature data corresponding to a first predetermined period and second feature data corresponding to a second predetermined period. Moreover, the sequential posture identification device includes a first generation unit that generates, by machine learning based on the first feature data, a dynamic/static activity identification model for identification of whether the subject is dynamic or static. The sequential posture identification device includes a second generation unit that generates, by machine learning based on the first feature data, a dynamic-activity identification model for identification of plural dynamic-activity patterns. What is more, the sequential posture identification device includes a third generation unit that generates, by machine learning based on the first feature data, a static-activity identification model for identification of plural static-activity patterns. The sequential posture identification device includes a first determination unit that determines, based on the dynamic/static activity identification model and the second feature data, whether the subject is dynamic or static in the second predetermined period. The sequential posture identification device includes a second determination unit that determines, based on the dynamic-activity identification model and the second feature data, a dynamic-activity pattern of the subject in the second predetermined period. The sequential posture identification device includes a third determination unit that determines, based on the static-activity identification model and the second feature data, a static-activity pattern of the subject in the second predetermined period. The sequential posture identification device includes an identification unit that identifies a posture and an activity of the subject in the second predetermined period, by combining together results of the determination by the first, second, and third determination units. The sequential posture identification device includes a generating unit that generates correspondence information associating the posture and activity identified by the identification unit, with biological signal information of the subject in the second predetermined period.

Therefore, the sequential posture identification device according to the first embodiment is able to promptly identify the posture and activity of the subject by performing the sequential machine learning of the acceleration information and the biological signal information transmitted sequentially from the wearable device. Further, since the sequential posture identification device according to the first embodiment generates the correspondence information associating the identified posture and activity with the biological signal information, the sequential posture identification device enables health management and disease prevention.

Further, the sequential posture identification device according to the first embodiment executes a sequential posture identification process by dividing the sequential posture identification process into a first step, at which "dynamic or static" is identified, and a second step, at which, what kind of dynamic activity or what kind of static activity the activity is, is identified. The biological signal information and acceleration information include both identification targets with high contrast and identification targets with low contrast. For example, "standing" and "sitting" have low contrast, and "ambulating" and "sitting" have high contrast. However, in the sequential posture identification process according to the first embodiment, the posture is identified in two steps by construction of a learning model through provision of also classification between "dynamic and static" as an upper layer of the identification. Therefore, identification between labels with high contrast does not influence identification between labels with low contrast (posture and activity). Further, by the two step identification, even if the labels are increased or decreased, the increase or decrease does not influence the identification of the other step, and thus increase or decrease of the labels is easily executed.

Further, the sequential posture identification device according to the first embodiment generates the correspondence information by associating the identified posture and activity with the biological signal information. Therefore, the sequential posture identification device according to the first embodiment enables continuous detection of change in the posture and activity of the subject in the subject's daily life, and evaluation through detection of the biological signal information and separation between the heart rate rising phase and heart rate falling phase caused due to different posture changes. For example, the sequential posture identification device according to the first embodiment enables distinguishment between a posture change, such as getting up or standing up, and a posture change, such as sitting down or lying down, by identification of the posture and activity. Accordingly, evaluation is enabled by division into: the heart rate rising phase reflecting the sympathetic function via the autonomic reflex due to the posture change, such as getting up or standing up; and the heart rate falling phase reflecting the vagal function due to the posture change, such as sitting down or lying down.

Further, the sequential posture identification device according to the first embodiment is able to generate an identification model highly dependent on a user, the identification model absorbing the body type and habits of posture of the individual, and enables accuracy of the identification process to be improved.

In the sequential posture identification device according to the first embodiment, the first generation unit, the second generation unit, and the third generation unit perform sequential learning by receiving input of feature data that are sequentially generated. That is, even if a user interrupts and ends machine learning of a posture after starting the machine learning for the posture, the sequential posture identification device is able to execute posture distinguishment based on postures and states of activity that have already been learnt. Further, since the sequential posture identification device uses a machine learning model, weighting of respective feature data is executed automatically. Thus, even if there is a difference between sets of feature data input with respect to a posture or a state of activity of the same label depending on subjects, the sequential posture identification device is able to construct identification models adapted to individuals easily. Furthermore, since the identification model is sequentially updated by execution of sequential learning, the user can interrupt or resume learning at any time.

Further, in contrast to a posture estimation method based on rules using a threshold or a decision tree, or based on learning utilizing a neutral network or a support vector machine (SVM), the sequential posture identification device according to the first embodiment enables accuracy of identification results to be improved by sequentially utilizing newly acquired data and increasing the learning accuracy. Furthermore, learning does not need to be started after acquisition of all of data needed in the learning, and even if the amount of data that have been acquired is small, the learning can be started.

Further, since the sequential posture identification device according to the first embodiment identifies a posture and an activity of a subject by using feature data acquired from biological signal information, in addition to acceleration information, accuracy of the identification result can be improved.

Further, in the sequential posture identification device according to the first embodiment, the feature data extraction unit extracts plural periods overlapping one another and having different lengths from one another from the first predetermined period, and extracts the first feature data for each of the extracted periods. That is, a set of feature data is extracted for each of the periods having different lengths, and is used in machine learning, and thus highly accurate posture identification can be realized.

Further, in the sequential posture identification device according to the first embodiment, the feature data extraction unit extracts the first and second feature data, based on: at least one of a maximum value, a minimum value, an average value, and a variance value, in a set of time series of acceleration information in a first period of the overlapping plural periods having different lengths; and at least one of a maximum value, a minimum value, an average value, and a variance value, of heartbeat intervals in a second period of the overlapping plural periods having different lengths.

As described above, the sequential posture identification device according to the first embodiment extracts feature data, not only from the acceleration information, but also from the biological signal information, and uses the extracted feature data in identification of a posture and an activity. Therefore, in contrast to a case where only the acceleration information is used, accuracy of the identification of the posture and activity can be improved. Further, by use of the biological signal information, the types of postures and activities that can be identified may be increased.

Further, in the sequential posture identification device according to the first embodiment, the feature data extraction unit extracts the first and second feature data, based further on at least one of: a vibration frequency along each axis of acceleration measured in the second period; and an average value and a variance value of vibration frequencies. As described above, by detailed extraction of feature data for each axis of acceleration, accuracy of identification of a posture and an activity can be improved.

Further, in the sequential posture identification device according to the first embodiment, the second period is longer than the first period. That is, by the extraction cycle of the feature data utilizing the biological signal information and the extraction cycle of the feature data utilizing the acceleration information being made different from each other, the lengths suitable for posture and activity identification are set. Therefore, accuracy of the posture and activity identification can be improved.

Further, in the sequential posture identification device according to the first embodiment, the processing by the first, second, and third generation units is executed in parallel with the processing by the first, second, and third determination units. Therefore, the learning process and the identification process can be executed in parallel with each other, and the parallel execution leads to improvement of the processing speed. Further, this also leads to prompt detection of abnormality in a subject.

Further, in the sequential posture identification device according to the first embodiment, the determined static-activity patterns are at least the standing position, the sitting position, and the recumbent position. Thus, the movement directions of the body of a subject can be determined by combination of the determination of the static-activity patterns, that is, the standing position, the sitting position, the recumbent position, and the like, and the determination of the two patterns, dynamic and static, and thus health management and disease prevention of the subject are enabled by association with the biological signal information.

Further, in the sequential posture identification device according to the first embodiment, the dynamic-activity patterns to be determined are at least ambulating, jumping, and stepping in place. Thus, the movement directions of the body of a subject can be determined by combination of the determination of the dynamic-activity patterns, that is, ambulating jumping, stepping, and the like, and the determination of the two patterns, dynamic and static, and thus health management and disease prevention of the subject are enabled by association with the biological signal information. Furthermore, types of dynamic activity can be finely classified and identified, and for example, ambulating where a subject is just simply walking in the subject's daily life, and walking as initiative exercise, can be distinguished from each other.

Further, the sequential posture identification device according to the first embodiment is able to generate information associating change in posture and activity of a subject in the subject's daily life with change in the biological signal information. In particular, the sequential posture identification device according to the first embodiment is able to associate a biological signal, such as the heart rate variability, with change in the posture and motion. Therefore, for example, the heart rate variability in a case without change in the posture and activity can be extracted and analyzed. In the case without change in the posture and activity, the main cause of heart rate variability is autonomic nerve fluctuation, such as a respiratory pulse. Therefore, by independent extraction of only the heart rate variability in the case without change in the posture and activity and analysis through separation between the heart rate rising phase and falling phase, autonomic function evaluation limited to the respiratory pulse can to be performed.

Further, the sequential posture identification device according to the first embodiment is able to execute the learning process and the identification process in parallel with each other by using sequential machine learning. Therefore, the sequential posture identification device according to the first embodiment is able to detect an abnormal value of a biological signal, such as heart rate variability under the same "posture and activity" conditions substantially in real time, at least within a delay time of about a few seconds.

Further, the sequential posture identification device according to the first embodiment is able to detect abnormality early by comparing data learnt by use of sequential machine learning with newly acquired data. For example, the sequential posture identification device enables prevention of falling, or prompt treatment, such as effective medicine administration, by detecting a syncopal attack, or indication of an attack, such as a sudden blood pressure change, or by detecting abnormality early in the attack.

Second Embodiment

Next, a technique for associating heart rate as biological signal information, with an identified posture or the like, by measurement and monitoring of the heart rate for autonomic function evaluation, will be described as a second embodiment. In the second embodiment also, a sequential posture identification process is executed similarly to that by the sequential posture identification device 20 according to the first embodiment, and thus details of the sequential posture identification process will be omitted in the following description.

(Significance of Association Between Heart Rate Variability Analysis and Posture)

As a premise, problems in heart rate analysis will be described first.

Heart rate analysis (heart rate variability analysis: HRV analysis) is widely used as an autonomic function measurement method. In heart rate analysis, analysis is generally performed by use of a large amount of data of one hundred or more pieces. However, resting heart rate and heart rate variability differ comparatively largely among individuals, and even if analysis is performed by use of many data, detection is difficult except for prominent dysautonomia. As fluctuation components influencing data on heart rate and heart rate variability, high frequency (HF) due to a respiratory pulse, or a Mayer wave of a blood pressure change, is reflected in the heart rate. It is difficult to normalize such fluctuation components in the same way with thresholds or the like by disregarding the individual differences.

However, it is not practical to perform analysis after acquisition of a large amount of heart rate data from a single subject for reflection of the individual differences, since sudden attacks or abnormality may not be dealt with thereby. Therefore, establishment of a technique for enabling prompt analysis reflecting individual differences by use of a small number of data acquired from a single subject is desirable.

Further, heart rate (average heart rate or the like) and amount of heart rate variability vary according to change in conditions, such as posture and presence or absence of physical activity. Therefore, it is desirable to perform data analysis for different conditions by associating variation in heart rate and amount of heart rate variability with conditions, such as posture and activity.

For example, various transitional reactions are caused in heart rate. For example, when a temporary reduction in arterial blood pressure occurs, baroreceptor reflex of the aortic arch or the carotid sinus is caused. In this case, after a transient increase in the heart rate (initial response) is caused, the heart rate is gently reduced (late response), and thereafter the heart rate is stabilized. On the contrary, via a reduction in the heart rate and a gradual increase in the heart rate following the reduction, the heart rate may transfer to periodic heart rate variability. There are various causes of these transitional reactions. For example, due to various causes, such as a posture change, an activity, and mental influence, transitional reactions are caused in the heart rate. Further, the strengths and response times of the transitional reactions differ depending on the causes.

Further, for example, FIG. 9 is a diagram for explanation of a case where similar changes occur in biological signal information for different postures and states of activity. As illustrated in FIG. 9, a reduction in heart rate variability due to tension upon being in standing position without a change in posture, and a reduction in heart rate variability due to exercise load with a change in motion both appear as decelerating phases.

However, conventionally, a method, in which heart rate variability data are collectively averaged, or are summed up, has been general. Therefore, it has been difficult to distinguish heart rate variability, such as transitional reactions occurring due to different causes, for every cause and to extract their respective features. Further, it has also been difficult to perform accurate analysis in consideration of: fluctuation characteristics of organisms caused in heart rate variability due to the same cause; and observation noise.

(Autonomic Function Information Acquisition Process According to Second Embodiment)

Based on the above, in an autonomic function information acquisition process according to the second embodiment, after a posture and an activity are identified by the sequential posture identification process, classification and grouping of heart rate data corresponding to respective conditions of posture and activity are performed. Further, in the autonomic function information acquisition process according to the second embodiment, the grouped heart rate data corresponding to the respective conditions are connected together after being subjected to a process, in which noise or the like is removed from the heart rate data. Furthermore, in the autonomic function information acquisition process according to the second embodiment, based on the grouped and connected heart rate data corresponding to the respective conditions, parameters of autonomic function evaluation under the respective conditions are calculated. Moreover, in the autonomic function information acquisition process according to the second embodiment, by execution of machine learning of biological signal information (heart rate data) sequentially acquired, information serving as a base line for evaluation of a state of autonomic function of a subject is acquired. In the autonomic function information acquisition process according to the second embodiment, based on the information serving as the base line, abnormality in the subject is promptly detected by analysis of biological signal information that is sequentially acquired newly.

(Example of Configuration of Autonomic Function Information Acquisition System According to Second Embodiment)

Figure 10:
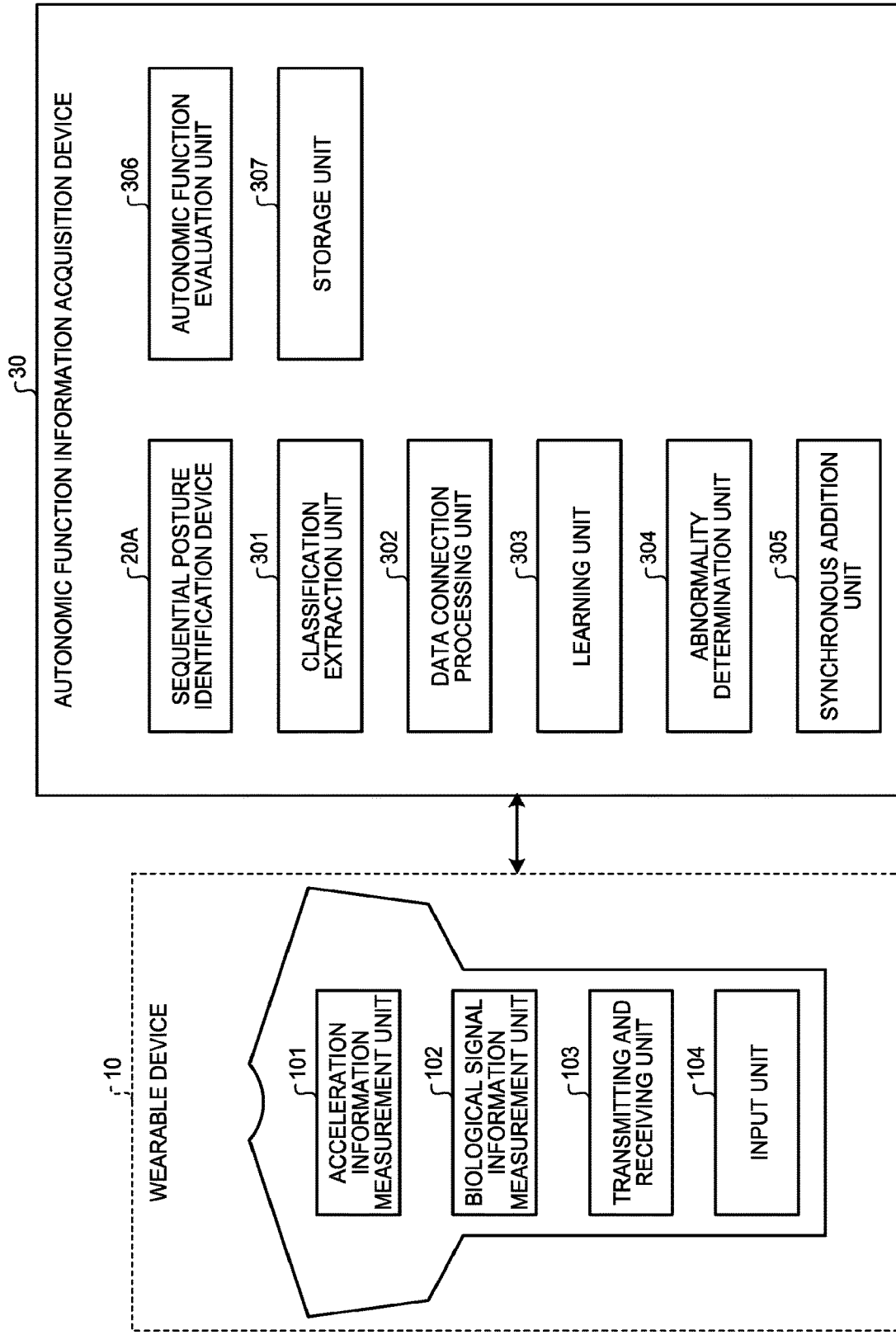
FIG. 10 is a schematic diagram illustrating an example of a configuration of an autonomic function information acquisition system according to a second embodiment.

FIG. 10 is a schematic diagram illustrating an example of a configuration of an autonomic function information acquisition system 2 according to the second embodiment. In FIG. 10, configurations and functions of the wearable device 10 and a sequential posture identification device 20A are similar to the configurations and functions of the wearable device 10 and the sequential posture identification device 20 of the first embodiment. However, the sequential posture identification device 20A illustrated in FIG. 10 does not include the generating unit 210 of the sequential posture identification device 20 illustrated in FIG. 1.

As illustrated in FIG. 10, the autonomic function information acquisition system 2 according to the second embodiment includes the wearable device 10, and an autonomic function information acquisition device 30. The wearable device 10 and the autonomic function information acquisition device 30 are communicatably connected to each other via a network.

The autonomic function information acquisition device 30 includes the sequential posture identification device 20A. In FIG. 10, the sequential posture identification device 20A is illustrated as a part of the autonomic function information acquisition device 30, but the sequential posture identification device 20A may be configured as a device separately bodied from the autonomic function information acquisition device 30. In this case, the sequential posture identification device 20A and the autonomic function information acquisition device 30 may be communicatably connected to each other via a network. The form of the connection is not particularly limited.

The wearable device 10 transmits acceleration information and biological signal information to the autonomic function information acquisition device 30. Since the configuration and functions of the wearable device 10 are the same as those of the wearable device 10 of the first embodiment, detailed description thereof will be omitted.

The sequential posture identification device 20A included in the autonomic function information acquisition device 30 identifies, from the received acceleration information and biological signal information, a posture and an activity of a subject whom the wearable device 10 is attached to. Since the method of identifying the posture and activity has been described in detail in the description of the first embodiment, description thereof will be omitted. However, as long as the posture and activity of the subject are able to be identified substantially in real time, information on the posture and activity acquired by use of another method may be used.

The autonomic function information acquisition device 30 extracts and analyzes heart rate data from the biological signal information transmitted from the wearable device 10. The autonomic function information acquisition device 30 extracts heart rate data corresponding to periods, in which the subject was in the same posture and activity, from the heart rate data. The heart rate data are, for example, information on the heart rate, or the like. The heart rate data are information, from which, based on the data, an index of autonomic function evaluation, such as the average heart rate, the heartbeat interval, the average heartbeat interval, the standard deviation of heart beat intervals, the variation coefficient of heartbeat intervals, the HF component, or the LF component, can be calculated.

The autonomic function information acquisition device 30 joins the extracted heart rate data together. The autonomic function information acquisition device 30 may perform adjustment of noise or the like in the heart rate data then. Thereby, the autonomic function information acquisition device 30 acquires information serving as a base line of the state of the heartbeat when the subject is in the same posture and activity. From the information serving as the base line, the autonomic function information acquisition device 30 calculates a parameter serving as an index of autonomic function evaluation. The calculated parameter can be used in autonomic function evaluation based on the heart rate data upon the same posture and activity.

Further, the autonomic function information acquisition device 30 performs sequential machine learning with respect to heart rate data, and performs comparison with heart rate data that are newly received from the wearable device 10. Thereby, the autonomic function information acquisition device 30 promptly detects any abnormality in the newly received heart rate data.

Further, the autonomic function information acquisition device 30 analyzes the state of heartbeat upon a particular change by synchronously adding heart rate data corresponding to periods, in which the same consecutive changes in posture and activity occurred. For example, the autonomic function information acquisition device 30 is able to selectively collect, synchronously add, and analyze heart rate data corresponding to a series of posture changes, for example, a subject stopping once when running (standing position and dynamic state), sitting down (sitting position and static state), and starting running again (standing position and dynamic state).

(Example of Configuration of Autonomic Function Information Acquisition Device 30 According to Second Embodiment)

By reference to FIG. 10, an example of a configuration of the autonomic function information acquisition device 30 will be described. The autonomic function information acquisition device 30 includes the sequential posture identification device 20A. Further, the autonomic function information acquisition device 30 includes a classification extraction unit 301, a data connection processing unit 302, a learning unit 303, an abnormality determination unit 304, a synchronous addition unit 305, an autonomic function evaluation unit 306, and a storage unit 307.

The classification extraction unit 301 associates biological signal information, that is, heart rate data, transmitted from the wearable device 10, with an identification result transmitted from the sequential posture identification device 20A, and extracts heart rate data for when the subject is in the same posture and state of activity. The classification extraction unit 301 extracts, from biological signal information chronologically acquired, parts corresponding to predetermined posture and activity. Thus, there is discontinuity among the extracted heart rate data. Further, the heart rate data extracted by the classification extraction unit 301 may include an abnormal value or noise. Therefore, for adjustment of the discontinuity or noise in the heart rate data, the extracted heart rate data are transmitted to the data connection processing unit 302. Details of the processing by the classification extraction unit 301 will be described later.

The data connection processing unit 302 acquires the heart rate data extracted by the classification extraction unit 301 and information on the posture and activity corresponding to the heart rate data. The data connection processing unit 302 then connects the heart rate data corresponding to the same posture and activity to one another. Upon the connection, the data connection processing unit 302 executes a data connection process, in which a discontinuous part where values of the connected heart rate data are not continuous, or noise in the heart rate data, is adjusted. Details of the data connection process will be described later. By the data connection process, the plural sets of heart rate data corresponding to the same posture and state of activity are connected to one another. The heart rate data that have been subjected to the data connection process are transmitted from the data connection processing unit 302 to the learning unit 303. Further, the heart rate data that have been subjected to the data connection process are transmitted from the data connection processing unit 302 to the storage unit 307 and stored therein. Every time new heart rate data are generated, the data stored in the storage unit 307 are updated. Further, from the heart rate data that have been subjected to the data connection process, the data connection processing unit 302 sequentially calculates, stores, and updates a statistic, such as an average value, a variance value, or a median point, of the heartbeat intervals under the respective conditions. The calculated value is used as a parameter of autonomic function evaluation.

The learning unit 303 executes machine learning of the heart rate data transmitted from the data connection processing unit 302. The machine learning is sequential machine learning, such as on-line learning.

The abnormality determination unit 304 detects any abnormality in newly acquired heart rate data by using results of the machine learning.

The synchronous addition unit 305 extracts plural sets of heart rate data corresponding to a series of changes in posture and state of activity, and synchronously adds together the plural sets of heart rate data by synchronizing predetermined time points thereof. Further, the synchronous addition unit 305 calculates, based on the heart rate data that have been synchronously added together, a numerical value to serve as a parameter of autonomic function evaluation.

The autonomic function evaluation unit 306 generates autonomic function evaluation information for notification of the statistic, such as the average value, the variance value, or the median point, which is acquired from the heart rate data corresponding to the respective conditions, the heart rate data having been subjected to the data connection process. Further, the autonomic function evaluation unit 306 generates autonomic function evaluation information for notification of the parameter of autonomic function evaluation calculated by the synchronous addition unit 305. Furthermore, the autonomic function evaluation unit 306 generates autonomic function evaluation information for notification of any abnormality when the abnormality determination unit 304 detects the abnormality. Moreover, similarly to the generating unit 210 included in the sequential posture identification device 20 according to the first embodiment, the autonomic function evaluation unit 306 generates autonomic function evaluation information chronologically associating a posture and a state of activity with biological signal information.

The storage unit 307 stores therein information used in the processing by the autonomic function information acquisition device 30, and information generated as a result of the processing. The storage unit 307 stores therein, for example, acceleration information and biological signal information transmitted from the wearable device 10. Further, the storage unit 307 stores therein the plural segments of heart rate data corresponding to the respective conditions extracted by the classification extraction unit 301, together with time stamps indicating the dates and times when the heart rate data were measured. Furthermore, the storage unit 307 stores therein the heart rate data that have been subjected to the data connection process by the data connection processing unit 302, together with the calculated parameter, in association with the respective conditions. Moreover, the storage unit 307 stores therein the heart rate data that have been synchronously added together by the synchronous addition unit 305, together with the calculated parameter, in association with the respective conditions. In addition, the storage unit 307 may store therein, as appropriate, the autonomic function evaluation information generated by the autonomic function evaluation unit 306.

(Example of Flow of Autonomic Function Information Acquisition Process According to Second Embodiment)

Figure 11:
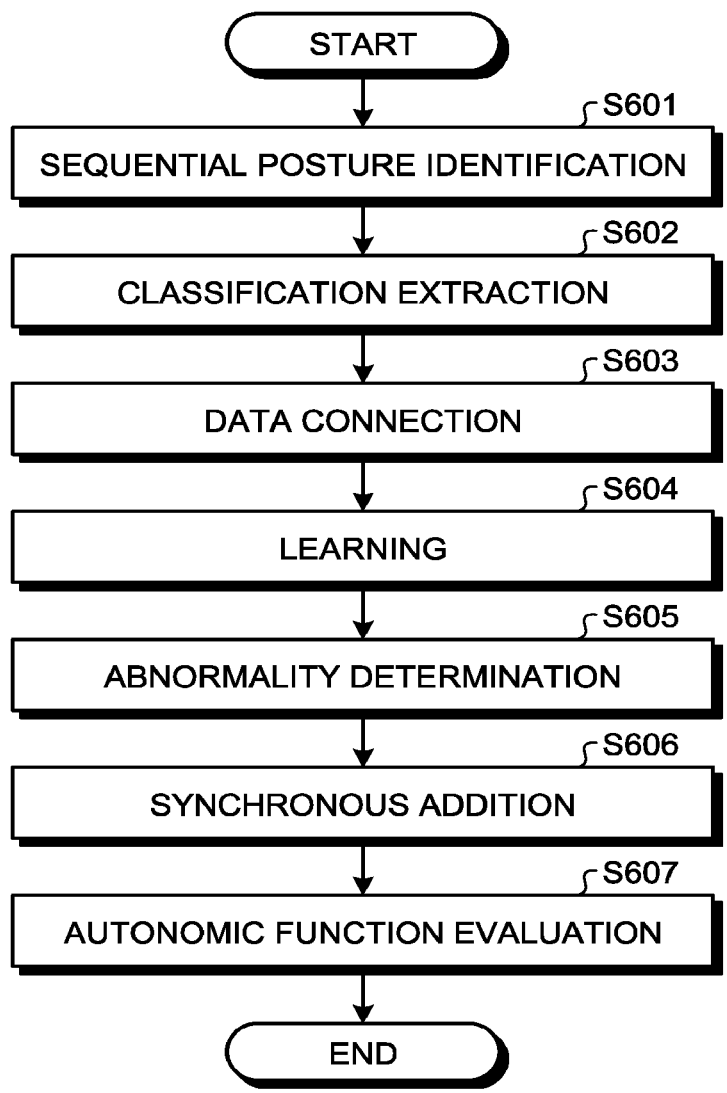
FIG. 11 is a flow chart illustrating an example of a flow of an autonomic function information acquisition process according to the second embodiment.

FIG. 11 is a flow chart illustrating an example of a flow of the autonomic function information acquisition process according to the second embodiment. As illustrated in FIG. 11, the autonomic function information acquisition device 30 of the second embodiment firstly executes the sequential posture identification process by the sequential posture identification device 20A (Step S601). Next, in association with information on a posture and an activity acquired as a result of the posture identification process, the classification extraction unit 301 classifies and extracts heart rate data for the same posture and activity (Step S602). The data connection processing unit 302 then deals with discontinuity or noise in the extracted heart rate data, and executes the data connection process (Step S603). The learning unit 303 executes machine learning of the heart rate data that have been subjected to the data connection process (Step S604). Based on results of the learning, the abnormality determination unit 304 executes abnormality detection on newly acquired heart rate data (Step S605). The synchronous addition unit 305 synchronously adds plural sets of heart rate data corresponding to the same consecutive changes in posture and activity by synchronizing predetermined time points thereof, and calculates a parameter of autonomic function evaluation (Step S606). The autonomic function evaluation unit 306 generates various pieces of autonomic function evaluation information, such as, for example, autonomic function evaluation information for notification of an abnormality detected by the abnormality determination unit 304 (Step S607). Thereby, the example of the autonomic function information acquisition process is ended.

In the example illustrated in FIG. 11, the determination result by the abnormality determination unit 304 is generated as the autonomic function evaluation information. However, not being limited thereto, the autonomic function evaluation unit 306 may output, as the autonomic function evaluation information, for example, the parameter of autonomic function evaluation generated by the synchronous addition unit 305. Which information is to be generated and output as the autonomic function evaluation information may be selected according to input of an instruction by a user.

Further, in FIG. 11, the processing from Step S603 to Step S606 has been described to be executed sequentially. However, practically, the device may be configured to execute an arbitrary part of the processing only when a user inputs an instruction. For example, the synchronous addition of Step S606 may be executed only when a user inputs an instruction. Further, the device may store therein consecutive changes in posture and motion to be subjected to a synchronous addition process in advance, and may execute the synchronous addition process every time the corresponding consecutive changes are detected and update the information stored in the storage unit 307.

(Classification Extraction Process)

Figure 12:
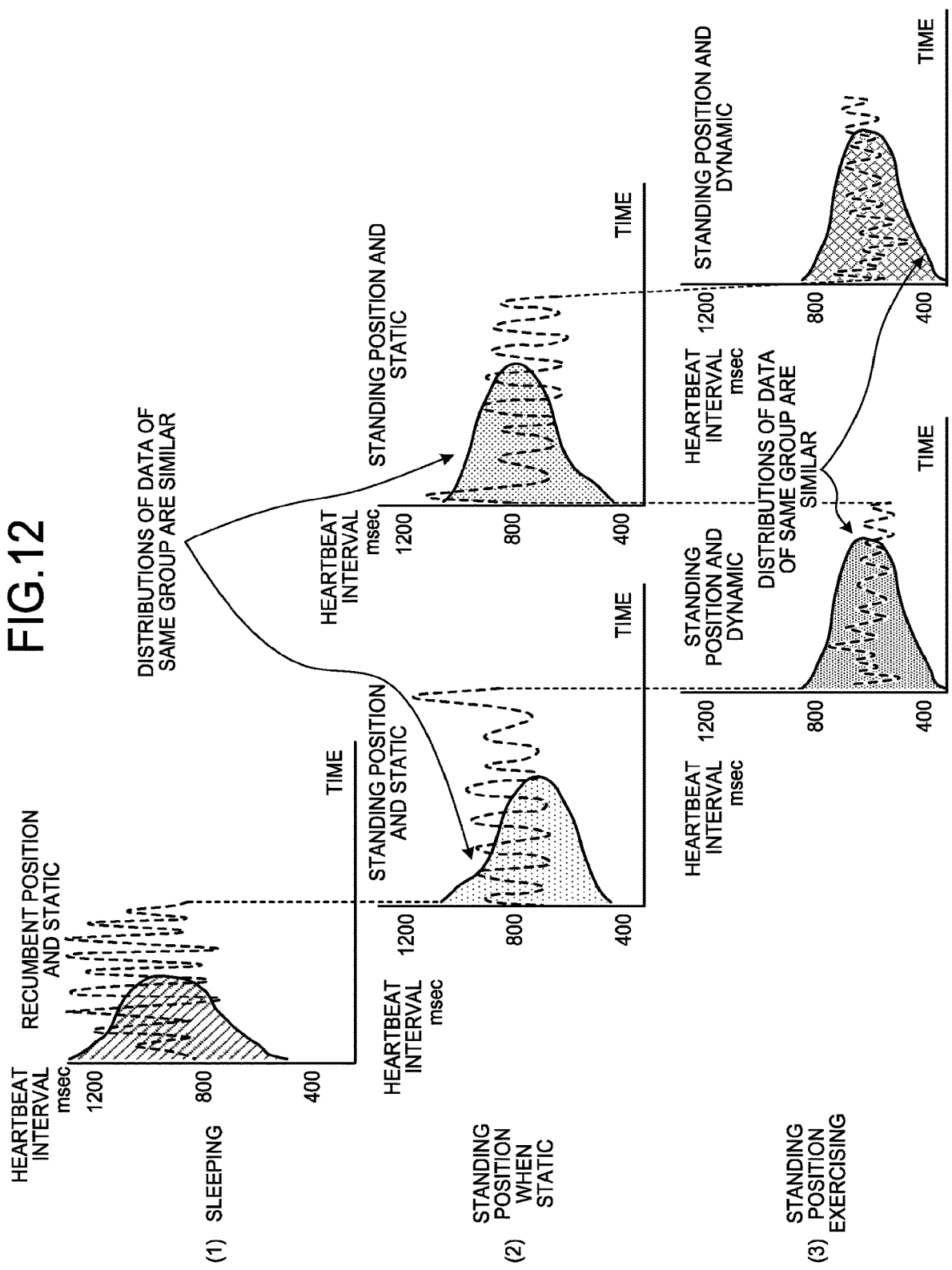
FIG. 12 is a diagram for explanation of classification (grouping) of biological signal information (heartbeat data) in the autonomic function information acquisition process according to the second embodiment.

Next, a classification extraction process executed by the classification extraction unit 301 will be described. FIG. 12 is a diagram for explanation of classification (grouping) of biological signal information (heart rate data) in the autonomic function information acquisition process according to the second embodiment. In FIG. 12, (1) illustrates a distribution of heartbeat intervals when a subject is sleeping (that is, "posture and activity" are "recumbent position and static"). In FIG. 12, (2) illustrates a distribution of heartbeat intervals when the subject is staying still while keeping standing (that is, "posture and activity" are "standing position and static"). Further, in FIG. 12, (3) illustrates a distribution of heartbeat intervals when the subject is exercising while standing (that is, "posture and activity" are "standing position and dynamic"). In FIG. 12, dotted lines indicate measured values of heartbeat intervals measured at respective time points, and solid lines indicate distributions of values of the heartbeat intervals measured.

As illustrated by (2) and (3) in FIG. 12, when the subject is in the same states of "posture" and "activity", the distributions of the heartbeat intervals are approximate to each other. At (2) in FIG. 12, the heartbeat interval variation over time differs between the right graph and the left graph, but the distributions of their data are approximate to each other. The same applies to (3) in FIG. 12.

The classification extraction unit 301 extracts heart rate data for when the subject is in the same states of "posture" and "activity". The classification extraction unit 301 thus acquires at least information on three types of "posture", which are "standing position", "sitting position", and "recumbent position", and information on two types of "activity", "static" and "dynamic". The classification extraction unit 301 then determines a period, in which each posture is in a stably held state (that is, there is no change in posture); and if there is a change in posture, a type of the change, a start time of the stably held state, and the like.

For example, in the example of FIG. 12, the classification extraction unit 301 accumulates heartbeat interval data corresponding to "standing position and static", in association with a classification, "standing position and static". Similarly, the classification extraction unit 301 accumulates heartbeat interval data corresponding to "standing position and dynamic", in association with a classification, "standing position and dynamic". The heartbeat interval data are stored with time stamps assigned thereto, such that which times the states of the subject indicated by the data are of can be known therefrom.

As described with respect to the first embodiment, in the sequential posture identification process, identification of a posture and an activity is sequentially executed. The determination of whether or not a posture is in the stably held state is executed promptly. For example, within a few seconds after a subject starts taking that posture, the determination of whether or not the posture is in the stably held state is executed. Further, even if a posture of a subject is changed, since the sequential posture identification device 20A is able to detect that change based on an inflection point of the acceleration information; in a short time, which is within a few seconds from the actual start of the change in posture, a start time of the change in posture is identified. Therefore, whether or not each posture is in the stably held state; an identified classification, such as "dynamic" or "static"; a start time of a change in posture, and the like are determined within a short time of a few seconds from the actual event occurrence, and thus the heart rate data are classified and accumulated.

By the classification extraction unit 301 continuously executing the above described classification extraction process, the stored heart rate data are accumulated and updated as required. The heart rate data extracted by the classification extraction unit 301 are sequentially stored in the storage unit 307.

(Data Connection Process)

Figure 13:
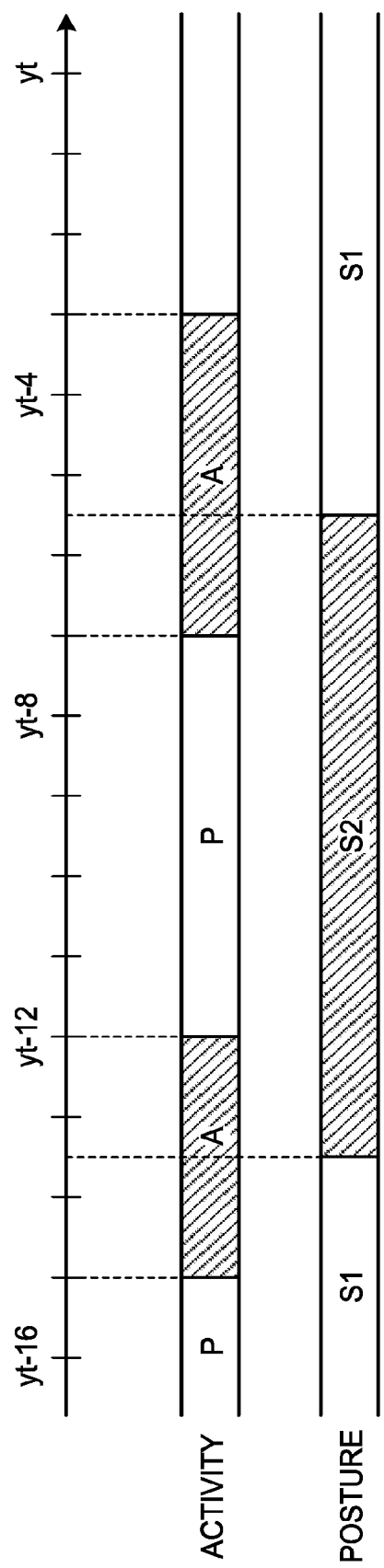
FIG. 13 is a diagram for explanation of a data connection process in the autonomic function information acquisition process according to the second embodiment.

Next, a data connection process executed by the data connection processing unit 302 will be described. FIG. 13 is a diagram for explanation of the data connection process in the autonomic function information acquisition process according to the second embodiment.

(Discontinuity in Data)

In FIG. 13, heartbeat interval data, which are biological signal information measured in the wearable device 10 from a time, "t-16", to a time, "t", are subjected to the data connection process. The heartbeat interval data acquired at the time, "t", are denoted by "yt". It will now be supposed that as a result of the sequential posture identification device 20A identifying posture and activity of a subject from the time, "t-16", to the time, "t", a change from a posture S1 (for example, the recumbent position) to a posture S2 (for example, the standing position) has occurred between a time, "t-14", and a time, "t-13". Further, it will also be supposed that a change from the posture S2 to the posture S1 has occurred between a time, "t-6", to a time, "t-5".

Further, it will also be supposed that at the time point of the time, "t-16", the subject is in a state of activity P ("static"), and at a time, "t-15", and a time, "t-7", a change from the state of activity P ("static") to a state of activity A ("dynamic") occurred. Furthermore, it will also be supposed that at a time, "t-12", and a time, "t-3", a change from the state of activity A ("dynamic") to the state of activity P ("static") occurred.

In this case, when the heart rate data are classified in association with a posture and an activity, a period corresponding to "recumbent position and dynamic" (S1 and A) is from the time, "t-15", to the time, "t-14", and from the time, "t-5", to the time, "t-3". Thus, continuous data of heartbeat intervals from the time, "t-15", to the time, "t-14", which are "yt-15" and "yt-14", and continuous data of heart beat intervals from the time, "t-5", to the time, "t-3", which are "yt-5", "yt-4", and "yt-3", are extracted. When these two sets of continuous data are attempted to be connected to each other, discontinuity is caused between the two sets of continuous data.

(Loss of Data)

Figure 14:
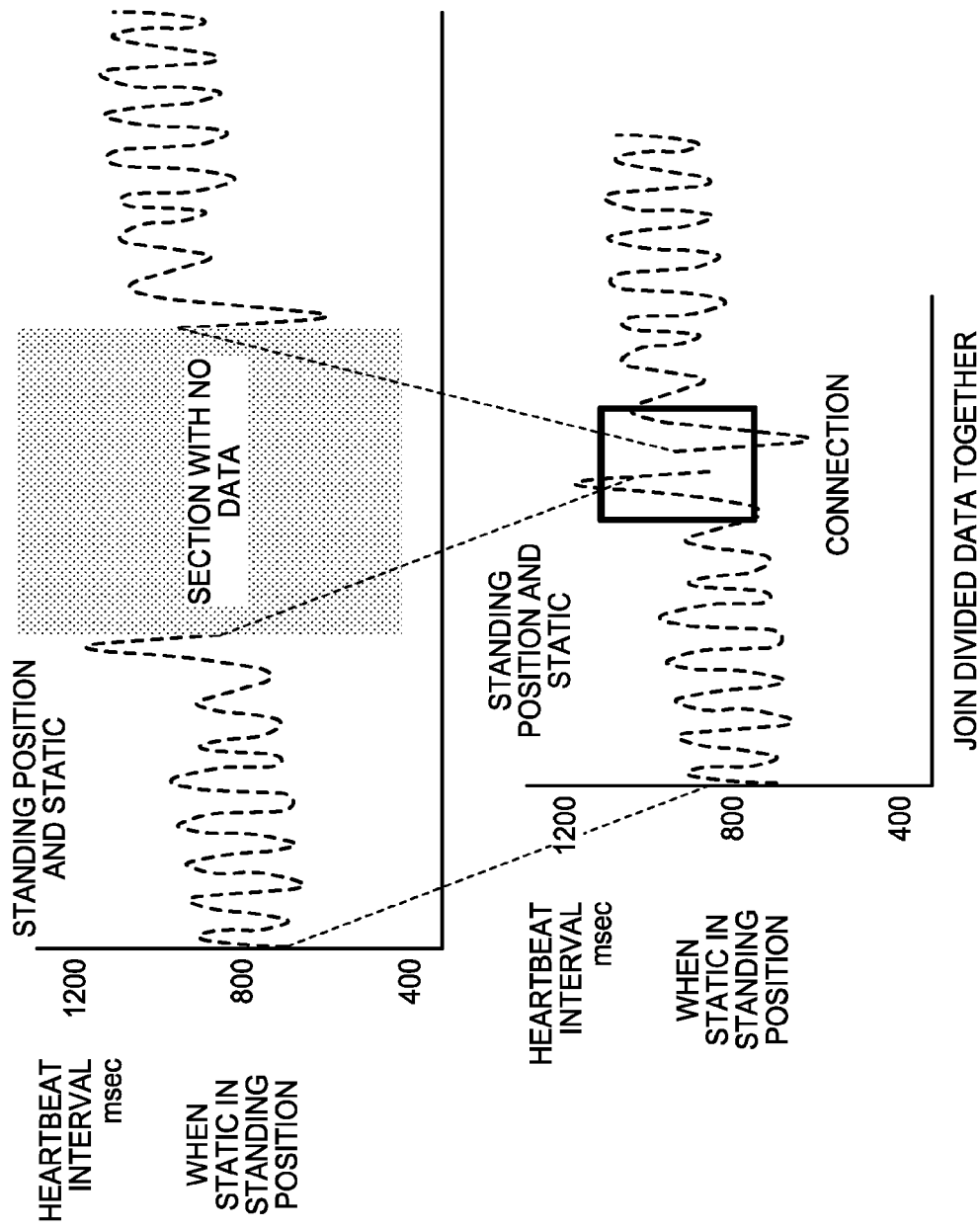
FIG. 14 is another diagram for explanation of the data connection process in the autonomic function information acquisition process according to the second embodiment.

Further, there may be a case where there is a loss in sets of heartbeat interval data acquired under the same conditions. FIG. 14 is another diagram for explanation of the data connection process in the autonomic function information acquisition process according to the second embodiment. FIG. 14 illustrates a case where there is a loss in sets of heartbeat interval data acquired under the same conditions, that is, conditions where a subject is in "standing position and static". For example, a data loss may continue in an unstable interval due to a transitional reaction of the autonomic nerve. When many data losses are caused in data, the number of data becomes deficient and appropriate learning and identification may not be executed.

Figure 15:
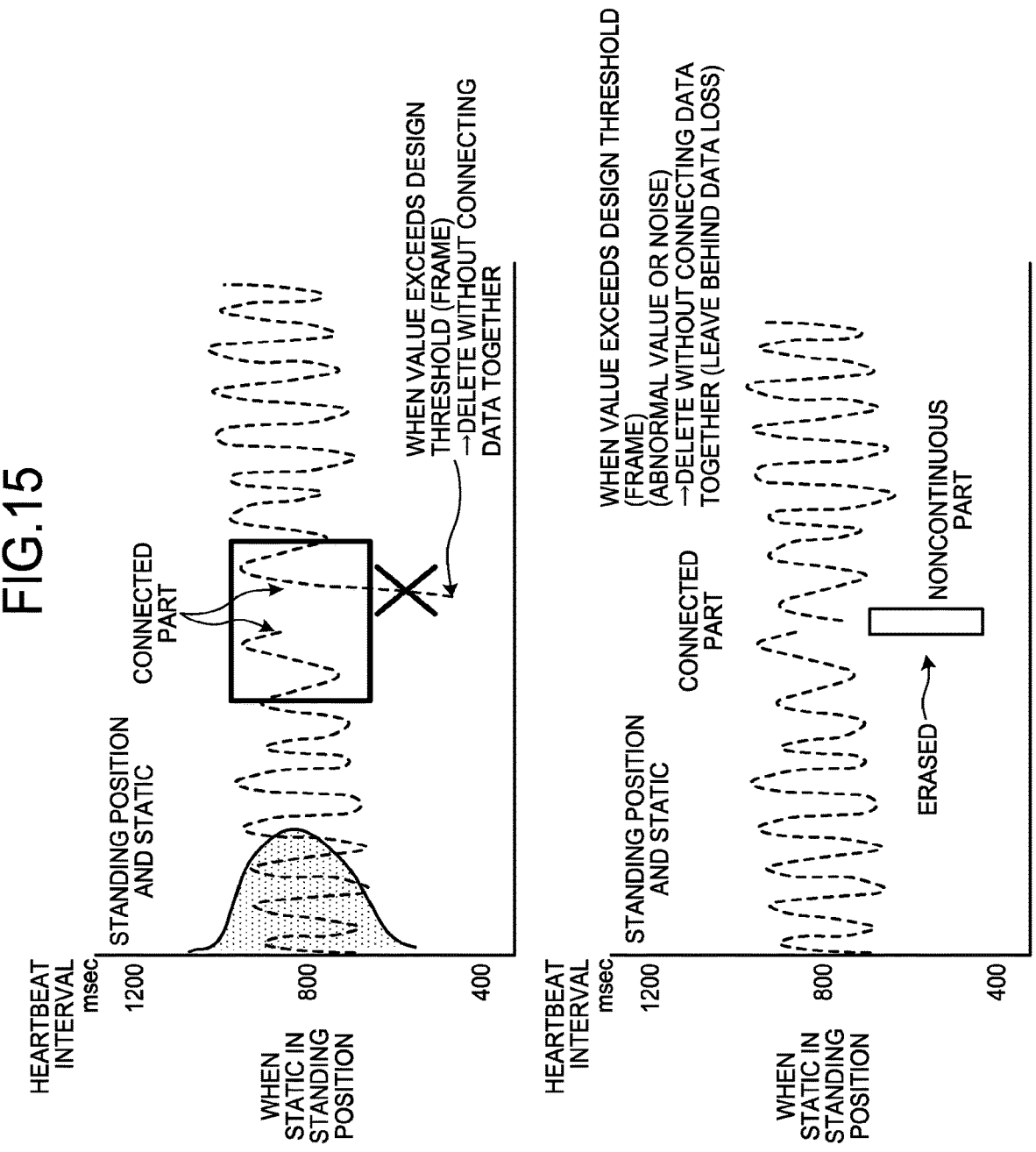
FIG. 15 is a diagram for explanation of a process, in which a threshold is used, in the data connection process in the autonomic function information acquisition process according to the second embodiment.
Figure 16:
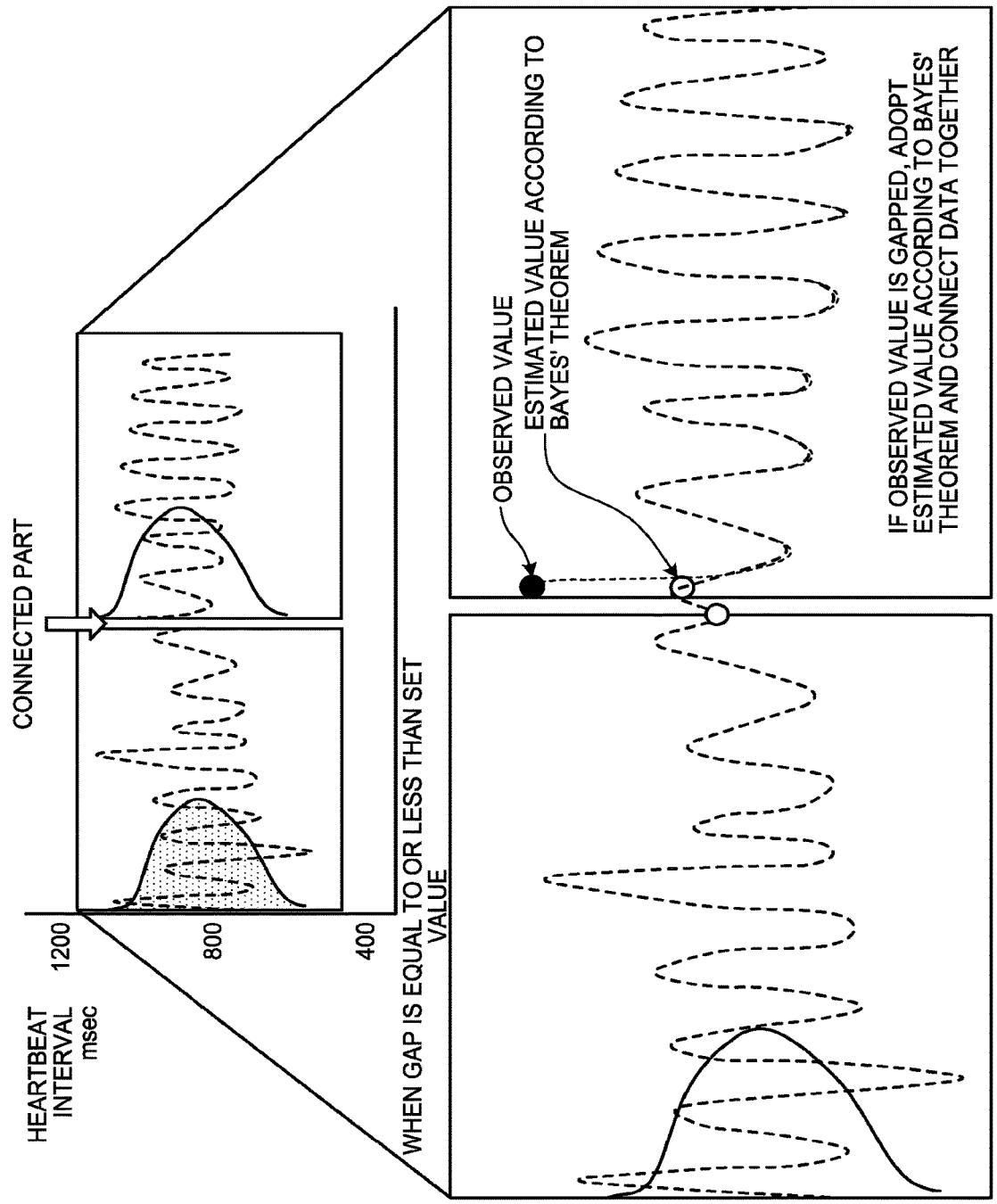
FIG. 16 is a diagram for explanation of a process, in which Bayes' theorem is used, in the data connection process in the autonomic function information acquisition process according to the second embodiment.

Therefore, in the second embodiment, a discontinuous part or loss in data is compensated, and the data are used by being regarded, as a whole, as continuous time series data. For example, FIG. 15 is a diagram for explanation of a process, in which a threshold is used, in the data connection process in the autonomic function information acquisition process according to the second embodiment. FIG. 16 is a diagram for explanation of a process, in which Bayes' theorem is used, in the data connection process in the autonomic function information acquisition method according to the second embodiment.

In the process illustrated in FIG. 15, a data loss and a value difference are caused between connected portions of two sets of data extracted correspondingly to the classification, "standing position and static", by the classification extraction unit 301. In the method illustrated in FIG. 15, for the heartbeat interval data corresponding to "standing position and static", a threshold is set in advance. In FIG. 15, the set threshold range is illustrated with a bold lined frame. If a value exceeding the set threshold appears in the connected portions, a portion corresponding to the value exceeding the threshold is deleted without being connected.

A deviated value exceeding the set threshold is considered to be caused by: mixture of noise upon measurement; an irregular pulse, such as extrasystole; or an unstable interval due to a transitional reaction. That is, a value exceeding the set threshold is highly likely to be an abnormal value or noise. Therefore, such a value is deleted from data to be stored, which are used in the autonomic function evaluation. If the value is included, as is, in the data to be used in the autonomic function evaluation, an appropriate evaluation parameter may not be acquired.

Although a threshold is used in the data connection process above, another statistical method may be used, other than the use of the fixed threshold as described above. For example, a nearest neighbor method, a method where a distribution is provisionally determined, a method where a test is repeated, or a method where a single-class identifier is used, may be used.

In the example illustrated in FIG. 16, although there is a difference between values of connected portions of two sets of data extracted by the classification extraction unit 301, an observed value is a value within a set threshold range. In this case, Bayes' theorem is applied thereto and a correct value is estimated. That is, from data that have been accumulated already, a prior distribution and a prior probability are found. Based on sets of data to be newly connected together, a posterior distribution is then found. The observed value is then corrected by the estimated value, and the two sets of data are connected to each other.

In the example of FIG. 16, although Bayes' theorem is used, a specific method of calculating the estimated value is not particularly limited, and any of various methods that use Bayes' theorem may be used, the various methods including Bayesian updating, Kalman filtering, and particle filtering. In addition, waveform interpolation by various kinds of estimation may be used. Further, multiple imputation, spline interpolation, or the like, may be used.

Further, the process, in which a normal value is estimated by use of Bayes' theorem, has been described as being executed for the connected portions of the sets of data, but the estimation process may be executed consecutively for all of time series data included in the same classification. Furthermore, after executing a process of estimating a correct value for heartbeat interval data sequentially acquired and added and for a posture identification result, data to be stored may be added or data update may be performed.

(Learning Process and Abnormality Determination Process)

Through the processing by the classification extraction unit 301 and the data connection processing unit 302, heart rate data are accumulated in association with respective conditions. Simultaneously with the acquisition and accumulation of the heart rate data serving as a base line, the learning unit 303 executes machine learning. The abnormality determination unit 304 then performs, based on results of the learning, comparison with newly acquired data, and detects any abnormality. For example, as the learning unit 303, a high speed machine learning device (linear or non-linear classifier) is used. For example, an identifier using a linear function or a nonlinear function is used. Further, a method, such as neighborhood query or clustering, may be used. Thereby, simultaneously with acquisition of heartbeat interval data, or within a short time after the acquisition, prompt abnormality detection can be realized. As to the machine learning, sequential machine learning, like the online learning used in the first embodiment, may be utilized. Thereby, there is no need for preparation of a large amount of data, and after a certain learning period, abnormality determination for the same posture and state of activity can be realized.

(Synchronous Addition Process)

The synchronous addition unit 305 executes the synchronous addition process separately from the processing by the data connection processing unit 302, the learning unit 303, and the abnormality determination unit 304. For example, the synchronous addition unit 305 generates, based on classifications of "posture and activity" identified by the sequential posture identification device 20A, a group of consecutive changes in posture and activity. The synchronous addition unit 305 then calculates a start time of a posture change from an angular change of the body, and performs synchronous addition of heart rate variability due to the posture change for each classification. For example, the synchronous addition unit 305 only extracts plural sets of data corresponding to a case where, for example, a change is caused in the heartbeat intervals as a result of a subject turning over while sleeping, and sets time points corresponding to time points, at which the subject turned over, as starting points of synchronization. The synchronous addition unit 305 then synchronously adds the plural sets of data, and calculates a parameter serving as an index of autonomic nerve evaluation for when the same posture change is caused.

Figure 17:
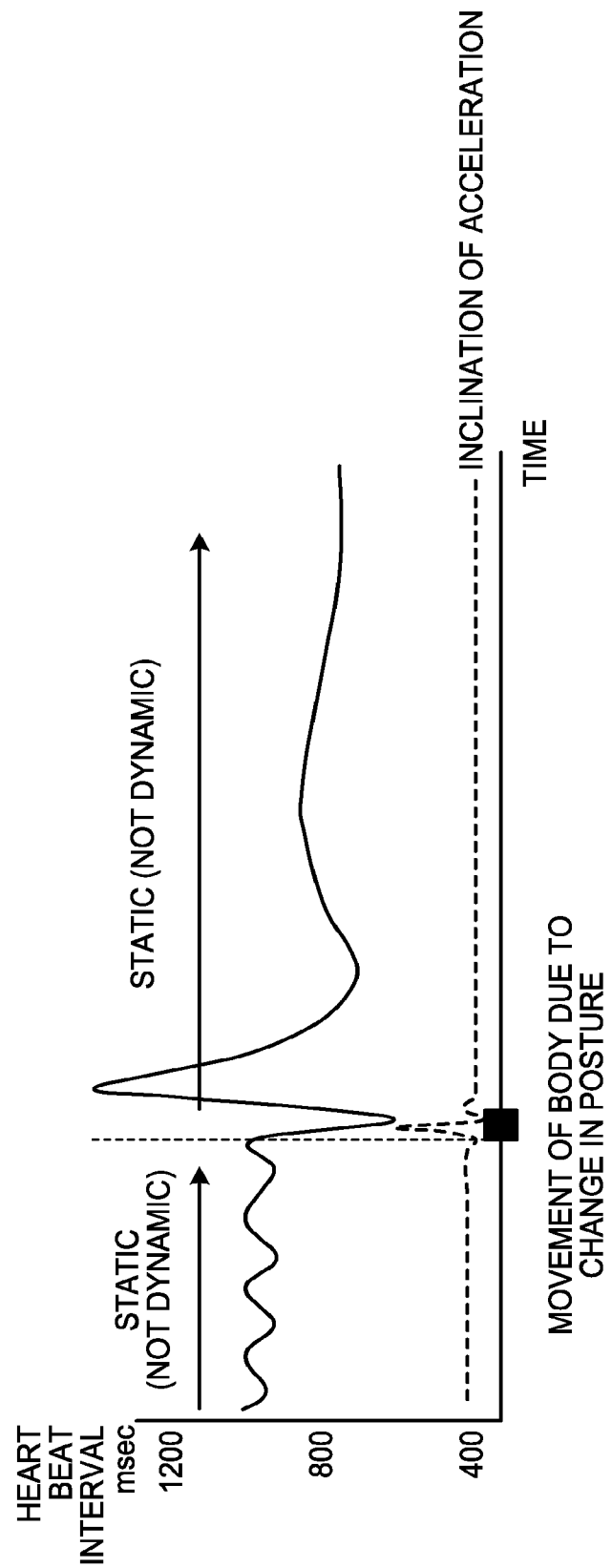
FIG. 17 is a diagram for explanation of a transitional reaction of heartbeat after a blood pressure decrease due to a change in posture of a subject.

For example, FIG. 17 is a diagram for explanation of a transitional reaction of the heart rate after a decrease of the blood pressure due to a posture change of a subject. As illustrated in FIG. 17, in a case where the subject turns over while sleeping and still keeps sleeping, the states of "posture and activity" change from "recumbent position and static" to "recumbent position and dynamic", and thereafter changes again to "recumbent position and static". The heart rate data (heartbeat intervals) measured from the subject in this case change, as illustrated in FIG. 17, from a stable state, via sudden decrease and increase. By addition of sets of heart rate data measured under the same conditions, heartrate data serving as a baseline for the same posture change can be acquired.

Figure 18:
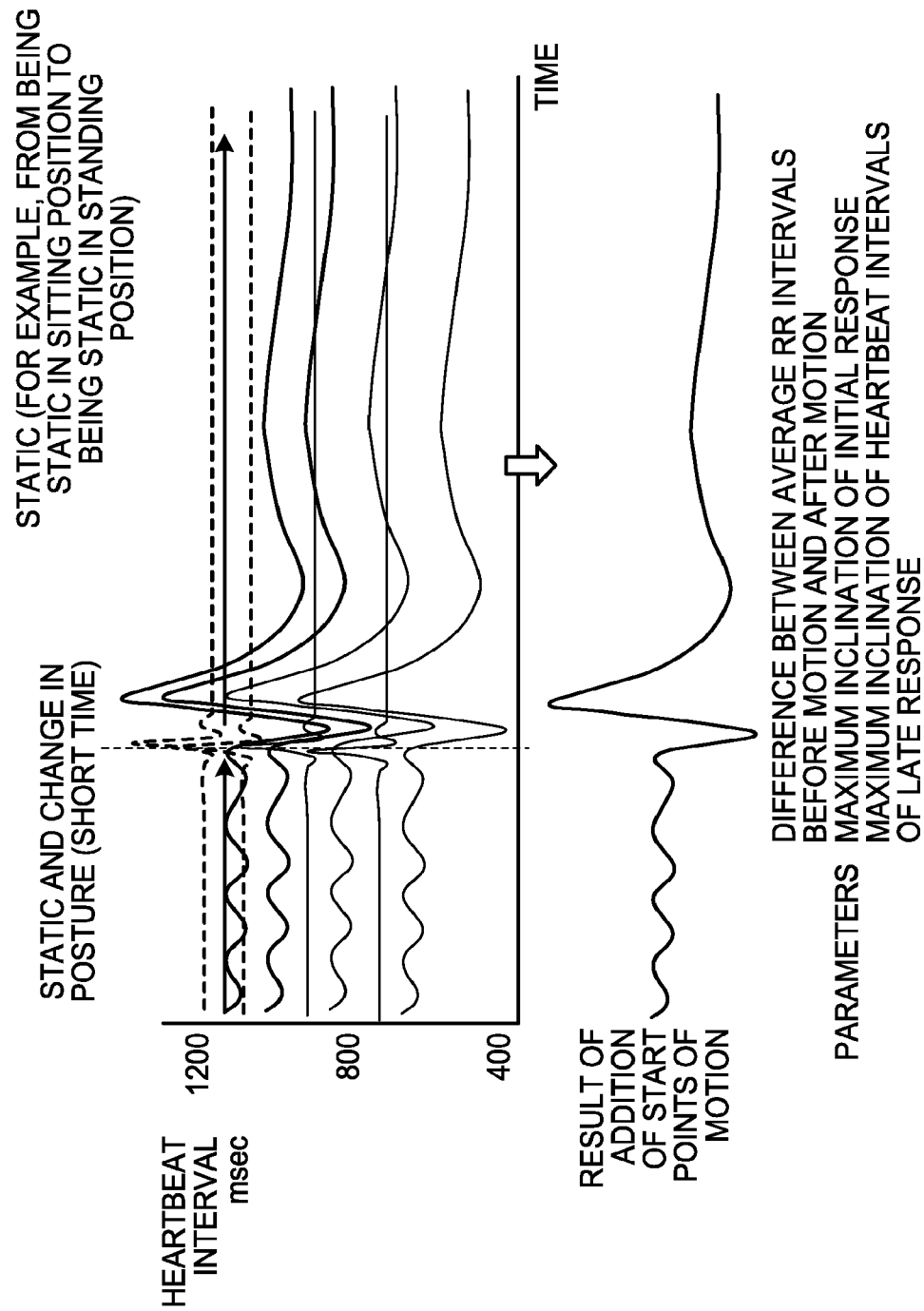
FIG. 18 is a diagram for explanation of a method of synchronously adding data for the transitional reaction of the heartbeat after the blood pressure decrease due to the change in posture of the subject, in the second embodiment.

FIG. 18 is a diagram for explanation of a method of synchronously adding sets of data for a transitional reaction of heart rate after a decrease of the blood pressure due to a posture change of a subject in the second embodiment. Firstly, based on a classification of posture and activity identified by the sequential posture identification device, heart rate data of: a change in posture; a start time of the change in posture; and intervals before and after the change in posture, during which the body is identified as not moving, are extracted. With a motion, that is, a posture change time point, being a base point, sets of heart rate data for when the same posture change occurs are synchronously added. That is, sets of variation data of heartbeat intervals respectively corresponding to the plural number of times of the change in posture are synchronously added together. As a parameter of autonomic nerve evaluation, a difference between average heartbeat intervals before and after the motion, the maximum inclination of the heartbeat intervals in the initial response, the maximum inclination of the heartbeat intervals in the late response, or the like is calculated.

Figure 19:
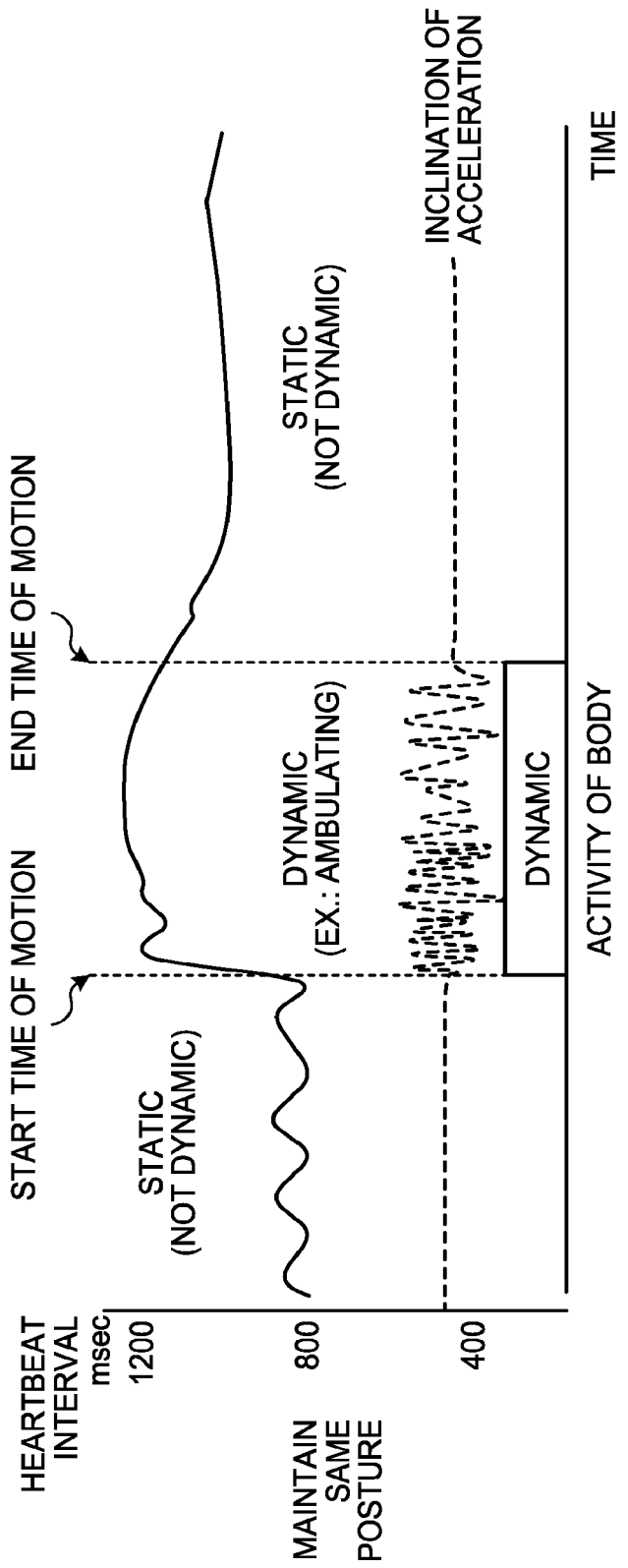
FIG. 19 is a diagram for explanation of a transitional reaction of heartbeat after a blood pressure increase due to a physical activity (exercise) of a subject.

With respect to the example in FIG. 17 and FIG. 18, an example, in which a change occurs in the biological signal information due to a change in posture, has been described. With respect to an example in FIG. 19 and FIG. 20, an example, in which a change occurs in biological signal information due to an activity, will be described. FIG. 19 is a diagram for explanation of a transitional reaction of the heart rate after an increase of the blood pressure due to a physical activity (exercise) of a subject.

In the example illustrated in FIG. 19, the subject changes from "static" state to "dynamic" state, and thereafter, changes to "static state". Throughout the period, in which the states of activity go through changes, the subject maintains the same posture. For example, a case where the subject changes from a state, "standing position and static", to "standing position and dynamic", for example, a running state, and returns to the state, "standing position and static" again, corresponds to the example in FIG. 19. In this case also, similarly to the example in FIG. 17, the blood pressure is increased due to the exercise and a transitional reaction is caused in the heartbeat intervals.

FIG. 20 is a diagram for explanation of a method of synchronously adding sets of data for the transitional reaction of the heart rate after the decrease of the blood pressure due to the physical activity (exercise) of the subject in the second embodiment. In the case of FIG. 20 also, similarly to the case of FIG. 18, plural sets of heart rate variability data corresponding to the same changes of states of activity are extracted and synchronously added together. That is, heart rate variability corresponding to periods, each in which the posture does not change and the states of activity change in order of "static", "dynamic", and "static", is extracted. Starting time points and ending time points of the periods of the "dynamic" state are determined. With the starting time points of the "dynamic" state being base points, the plural sets of heart rate variability data are synchronously added together. Further, with the ending time points of the "dynamic" state being base points, the plural sets of heart rate variability data are synchronously added together. Based on the data acquired as described above, a parameter of autonomic function evaluation according to the activity is acquired, and thus the autonomic function evaluation may be performed.

The synchronous addition is respectively performed with the starting time points or the ending time points being the base points, because duration times of the "dynamic" state are not uniform, and thus addition is to be executed by synchronization of the rising phases or the falling phases.

As the parameter of the autonomic function, when the starting time points are made the base points, the maximum inclination of the rising phase, the average heart rate after the rise, the difference between the average heart rates before the motion and during the motion, or the difference between the average heartbeat intervals before the motion and during the motion, may be used. Further, when the ending time points are made the base points, the maximum inclination of the falling phase, the average heart rate after the fall, the difference between the average heart rates during the motion and after the ending of the motion, or the difference between the average heartbeat intervals during the motion and after the ending of the motion, may be used.

Effects of Second Embodiment

As described above, an autonomic function evaluation device according to the second embodiment includes an acceleration information measurement unit, which is provided in a wearable device, and measures acceleration information of motion of a subject whom the wearable device is attached to. Further, the autonomic function evaluation device according to the second embodiment includes a biological signal information measurement unit, which is provided in the wearable device, and measures biological signal information of the subject. Furthermore, the autonomic function evaluation device according to the second embodiment includes an identification unit that identifies, by executing sequential machine learning for acceleration information and biological signal information in a first predetermined period, a posture and an activity of the subject in a second predetermined period. Moreover, the autonomic function evaluation device according to the second embodiment includes an extraction unit that extracts biological signal information corresponding to a combination of the same posture and activity identified by the identification unit. What is more, the autonomic function evaluation device according to the second embodiment includes a calculation unit that calculates a parameter of autonomic function evaluation from the biological signal information extracted by the extraction unit and corresponding to the combination of the same posture and activity.

As described above, an autonomic function information acquisition process according to the second embodiment enables a parameter to be extracted after classification of heart rate data corresponding to conditions of posture and activity. Accordingly, heart rate variabilities caused by different causes can be distinguished from one another and analyzed.

Further, in an autonomic function information acquisition device according to the second embodiment: the biological signal information measurement unit measures, as the biological signal information, heart rate data of the subject; the extraction unit extracts heart rate data corresponding to the combination of the same posture and activity; and the calculation unit calculates, as the parameter, at least one of an average value, a variance value, and a median point of the heart rate data extracted by the extraction unit.

Therefore, the evaluation parameter can be set by association of information on the heart rate, which is generally utilized in evaluation of the autonomic function, with states of the posture and activity, and analysis thereof. Accordingly, the autonomic function information acquisition process according to the second embodiment enables evaluation of the autonomic function based on data reflecting the individual habits and physiological properties acquired from each subject.

Further, the autonomic function information acquisition device according to the second embodiment further includes a connection unit that connects the heart rate data extracted by the extraction unit and corresponding to the combination of the same posture and activity into a group of data, and the connection unit statistically calculates, when a difference between values of connected portions of the connected heart rate data is less than a predetermined threshold, an estimated value that corrects the difference, and connects together the heart rate data that have been corrected by the estimated value.

Further, the autonomic function information acquisition device according to the second embodiment further includes a connection unit that connects the heart rate data extracted by the extraction unit and corresponding to the combination of the same posture and activity into a group of data, and when a difference between values of connected portions of the connected heart rate data is equal to or larger than a predetermined threshold, the connection unit connects the heart rate data together after deleting a value exceeding the predetermined threshold.

Therefore, the autonomic function information acquisition process according to the second embodiment enables, even if the amount of heart rate data acquired from the subject is small, heart rate data acquired under the same conditions to be connected together and analyzed. Therefore, accurate analysis by use of a small amount of data can be realized.

Further, in the autonomic function information acquisition device according to the second embodiment: the biological signal information measurement unit measures, as the biological signal information, heart rate data of the subject; the extraction unit extracts plural sets of heart rate data corresponding to periods corresponding to the same consecutive changes in posture and activity; and the calculation unit synchronously adds, by synchronization of starting time points or ending time points of a change in posture or activity in the plural sets of heart rate data extracted by the extraction unit, the plural sets of heart rate data together, and calculates a parameter from the synchronously added data. Therefore, the autonomic function information acquisition process according to the second embodiment enables a heart rate variability due to a change in posture and activity to be analyzed. Further, heart rate data corresponding to a particular combination of or change in posture and activity can be separated and analyzed. Accordingly, precise autonomic function evaluation according to states of subjects can be realized.

Further, in the autonomic function information acquisition device according to the second embodiment: the extraction unit extracts plural sets of heart rate data corresponding to periods corresponding to the same consecutive changes in posture and activity, each of the periods being a period, in which a subject changed the posture and the body of the subject before and after a time point of the change in posture is static; and the calculation unit calculates, as a parameter, at least one of a difference between average heartbeat intervals before and after the time point of the change in posture, the maximum inclination of the heartbeat intervals in an initial response, and the maximum inclination of the heartbeat intervals in the late response. Therefore, the autonomic function information acquisition process according to the second embodiment enables a heart rate variability due to a change in posture and activity to be analyzed. Further, heart rate data corresponding to a particular combination of or change in posture and activity can be separated and analyzed. Accordingly, precise autonomic function evaluation according to states of subjects can be realized.

Further, in the autonomic function information acquisition device according to the second embodiment: the extraction unit extracts plural sets of heart rate data corresponding to periods corresponding to the same consecutive changes in posture and activity, each of the periods being a period, in which the subject changes from a static state to a dynamic state and thereafter returns to the static state again, and during which the posture of the subject does not change; and the calculation unit synchronously adds the plural sets of heart rate data by synchronization of starting time points of the dynamic state, and calculates, as a parameter, at least one of the maximum inclination of a rising phase of the heart rate, an average heart rate after the rise, and a difference between average heart rates or average heartbeat intervals before start of the dynamic state and during the dynamic state. Therefore, the autonomic function information acquisition process according to the second embodiment enables a heart rate variability due to a change in posture and activity to be analyzed. Further, heart rate data corresponding to a particular combination of or change in posture and activity can be separated and analyzed. Accordingly, precise autonomic function evaluation according to states of subjects can be realized.

Further, in the autonomic function information acquisition device according to the second embodiment: the extraction unit extracts plural sets of heart rate data corresponding to periods corresponding to the same consecutive changes in posture and activity, each of the periods being a period, in which the subject changes from a static state to a dynamic state and thereafter returns to the static state again, and during which the posture of the subject does not change; and the calculation unit synchronously adds together the plural sets of heart rate data by synchronization of ending time points of the dynamic state, and calculates, as a parameter, at least one of the maximum inclination of a heart rate falling phase, an average heart rate after the fall, and a difference between average heart rates or average heartbeat intervals during the dynamic state and after ending of the dynamic state. Therefore, the autonomic function information acquisition process according to the second embodiment enables a heart rate variability due to a change in posture and activity to be analyzed. Furthermore, heart rate data corresponding to a particular combination of or change in posture and activity can be separated and analyzed. Accordingly, precise autonomic function evaluation according to states of subjects can be realized.

Further, the autonomic function information acquisition device according to the second embodiment further includes: a learning unit that executes machine learning based on association between posture and activity identified by the identification unit and biological signal information; and an abnormality detection unit that detects, based on results of the machine learning by the learning unit, any abnormality in a subject from the acceleration information and the biological signal information measured by the acceleration information measurement unit and the biological signal information measurement unit.

Accordingly, simultaneously with or within a short time from data acquisition, abnormality detection can be performed promptly (sequentially or within a delay of a few seconds) by comparison with accumulated data. Further, via a certain learning time, highly accurate abnormality determination can be realized, particularly for the same posture in the static state.

Further, in the autonomic function information acquisition device according to the second embodiment, the first predetermined period and the second predetermined period overlap each other at least partially. That is, the learning process and the identification process can be executed in parallel with each other, and continuous monitoring of a subject and machine learning can be realized in parallel with each other.

(Program)

Figure 21:
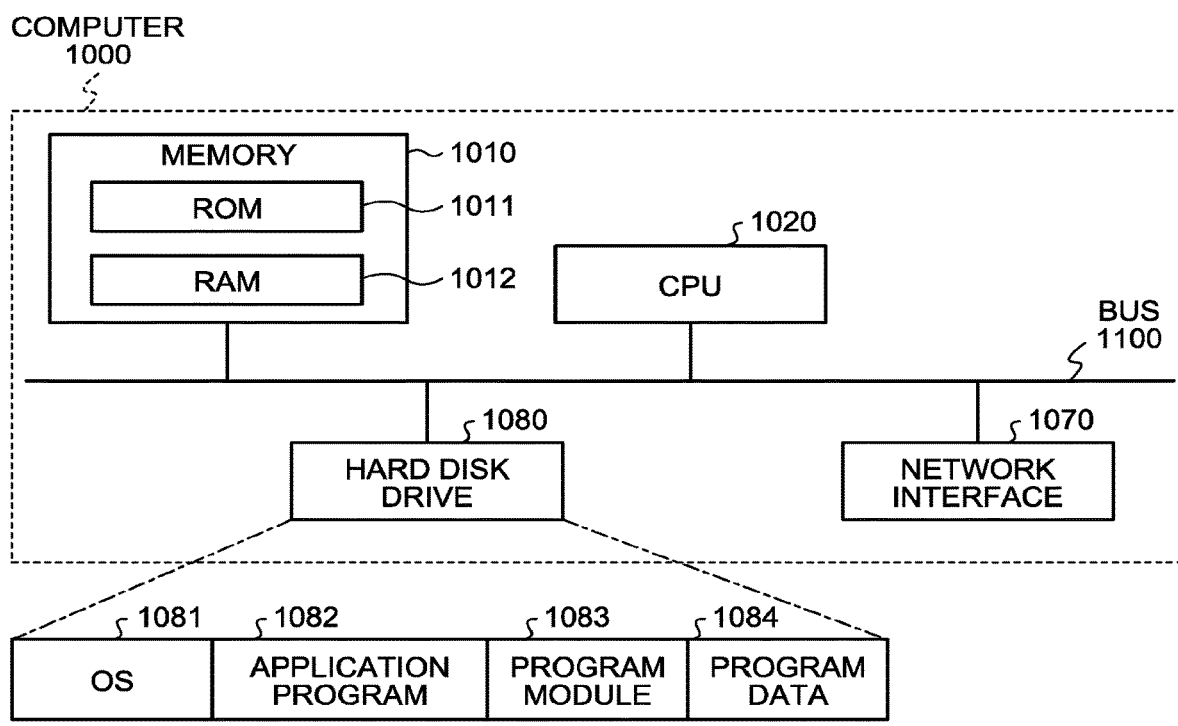
FIG. 21 is a diagram illustrating that information processing by a sequential posture identification program and an autonomic function information acquisition program according to the disclosed techniques are tangibly realized by use of a computer.

FIG. 21 is a diagram illustrating that information processing by a sequential posture identification program and an autonomic function information acquisition program according to the disclosed techniques is tangibly realized by use of a computer. As illustrated in FIG. 21, a computer 1000 has, for example, a memory 1010, a central processing unit (CPU) 1020, a hard disk drive 1080, and a network interface 1070. These respective units of the computer 1000 are connected to one another via a bus 1100.

The memory 1010 includes, as illustrated in FIG. 21, a read only memory (ROM) 1011 and a random access memory (RAM) 1012. The ROM 1011 stores therein, for example, a boot program, such as Basic Input Output System (BIOS).

As illustrated in FIG. 21, the hard disk drive 1080 stores therein, for example, an OS 1081, an application program 1082, a program module 1083, and program data 1084. That is, the sequential posture identification program and the autonomic function information acquisition program according to the disclosed embodiments are stored, as the program module 1083, in which commands executed by a computer are described, in, for example, the hard disk drive 1080. For example, the program module 1083 is stored in the hard disk drive 1080, the program module 1083 having respective processes described therein, through which information processing that is the same as that of the sequential posture identification device 20 and the autonomic function information acquisition device 30 is executed.

Further, like the data stored in the storage unit 307, data used in the information processing by the sequential posture identification program and the autonomic function information acquisition program are stored, as the program data 1084, in, for example, the hard disk drive 1080. The CPU 1020 then reads the program module 1083 or the program data 1084 stored in the hard disk drive 1080, as necessary, into the RAM 1012, and executes various processes.

The program module 1083 and the program data 1084 related to the sequential posture identification program and the autonomic function information acquisition program are not necessarily stored in the hard disk drive 1080. For example, the program module 1083 or the program data 1084 may be stored in an attachable and detachable storage medium. In this case, the CPU 1020 reads out the data via the attachable and detachable storage medium, such as a disk drive. Further, similarly, the program module 1083 or the program data 1084 related to the sequential posture identification program and the autonomic function information acquisition program may be stored in another computer connected via a network (local area network (LAN), wide area network (WAN), or the like). In this case, the CPU 1020 reads out the various data by accessing the other computer via the network interface 1070.

[Others]

The sequential posture identification program and the autonomic function information acquisition program described in the embodiments may be distributed via a network, such as the Internet. Further, the sequential posture identification program and the autonomic function information acquisition program may be recorded in a computer readable recording medium, such as a hard disk, a flexible disk (FD), a CD-ROM, an MO, or a DVD, and executed by being read out from the recording medium by a computer.

Of the respective processes described in the embodiments, all or a part of any process described as being executed automatically may be executed manually, or all or a part of any process described as being executed manually may be executed automatically by a known method. In addition, the procedures, control processes, specific names, and information including various data and parameters, which have been described above and illustrated in the drawings, may be arbitrarily modified unless otherwise particularly stated.

The above described embodiments and their modifications are included in the techniques disclosed by the present application, and are also included in the inventions described in the claims and equivalent scope thereof.

REFERENCE SIGNS LIST

1 SEQUENTIAL POSTURE IDENTIFICATION SYSTEM
10 WEARABLE DEVICE
101 ACCELERATION INFORMATION MEASUREMENT UNIT
102 BIOLOGICAL SIGNAL INFORMATION MEASUREMENT UNIT
103 TRANSMITTING AND RECEIVING UNIT
2 AUTONOMIC FUNCTION INFORMATION ACQUISITION SYSTEM
20 SEQUENTIAL POSTURE IDENTIFICATION DEVICE
201 TRANSMITTING AND RECEIVING UNIT
202 FEATURE DATA EXTRACTION UNIT
203 FIRST GENERATION UNIT
204 SECOND GENERATION UNIT
205 THIRD GENERATION UNIT
206 FIRST DETERMINATION UNIT
207 SECOND DETERMINATION UNIT
208 THIRD DETERMINATION UNIT
209 IDENTIFICATION UNIT
210 GENERATING UNIT
211 INPUT UNIT
30 AUTONOMIC FUNCTION INFORMATION ACQUISITION DEVICE
301 CLASSIFICATION EXTRACTION UNIT
302 DATA CONNECTION PROCESSING UNIT
303 LEARNING UNIT
304 ABNORMALITY DETERMINATION UNIT
305 SYNCHRONOUS ADDITION UNIT
306 AUTONOMIC FUNCTION EVALUATION UNIT
307 STORAGE UNIT

The invention claimed is:

1. A sequential posture identification device, comprising:
a wearable device that is configured to be attached to a trunk of a subject;
an acceleration sensor that is provided in the wearable device, and measures acceleration information of motion of the subject whom the wearable device is attached to;
a biological signal information sensing device that is provided in the wearable device, and measures biological signal information of the subject; and
processing circuitry configured to
extract, from the acceleration information and the biological signal information, first feature data corresponding to a first predetermined period and second feature data corresponding to a second predetermined period;
perform a first generation process that generates, by machine learning based on the first feature data, a dynamic/static activity identification model for identification of whether the subject is involved in a dynamic activity or in a static activity;
perform a second generation process that generates, by machine learning based on the first feature data, a dynamic-activity identification model for identification of plural dynamic-activity patterns;
perform a third generation process that generates, by machine learning based on the first feature data, a static-activity identification model for identification of plural static-activity patterns;
perform a first determination process that determines, based on the dynamic/static activity identification model and the second feature data, whether the subject is involved in a dynamic activity or in a static activity in the second predetermined period;
perform a second determination process that determines, based on the dynamic-activity identification model and the second feature data, a dynamic-activity pattern of the subject in the second predetermined period;
perform a third determination process that determines, based on the static-activity identification model and the second feature data, a static-activity pattern of the subject in the second predetermined period;
identify a posture and an activity of the subject in the second predetermined period, by combining together results of the determination by the first, second, and third determination units; and
generate correspondence information associating between the posture and activity identified by the identification unit and biological signal information of the subject in the second predetermined period.

2. The sequential posture identification device according to claim 1, wherein the processing circuitry extracts, from the first predetermined period, plural periods overlapping one another and having different lengths, and extracts the first feature data for each of the extracted periods.

3. The sequential posture identification device according to claim 2, wherein the processing circuitry extracts the first and second feature data, based on: at least one of a maximum value, a minimum value, an average value, and a variance value, in a set of time series of acceleration information in a first period of the plural periods overlapping one another and having different lengths; and at least one of a maximum value, a minimum value, an average value, and a variance value, of heartbeat intervals in a second period of the plural periods overlapping one another and having different lengths.

4. The sequential posture identification device according to claim 3, wherein the processing circuitry extracts the first and second feature data, based further on at least one of: a vibration frequency along each axis of acceleration measured in the second period; an average value of vibration frequencies; and a variance value of the vibration frequencies.

5. The sequential posture identification device according to claim 3, wherein the second period is longer than the first period.

6. The sequential posture identification device according to claim 1, wherein processing by the first, second, and third generation processes is executed in parallel with processing by the first, second, and third determination processes.

7. The sequential posture identification device according to claim 1,
wherein the static-activity patterns are at least a standing position, a sitting position, and a recumbent position.

8. The sequential posture identification device according to claim 1, wherein the dynamic-activity patterns are at least ambulating, jumping, and stepping in place.

9. A sequential posture identification method, including:
a reception step of receiving respectively, from an acceleration information measurement unit and a biological signal information measurement unit that are provided in a wearable device that is configured to be attached to a trunk of a subject, acceleration information on motion of the subject whom the wearable device is attached to, and biological signal information of the subject;
a feature data extraction step of extracting, from the acceleration information and the biological signal information, first feature data corresponding to a first predetermined period and second feature data corresponding to a second predetermined period;
a first generation step of generating, by machine learning based on the first feature data, a dynamic/static activity identification model for identification of whether the subject is involved in a dynamic activity or in a static activity;
a second generation step of generating, by machine learning based on the first feature data, a dynamic-activity identification model for identification of plural dynamic-activity patterns;
a third generation step of generating, by machine learning based on the first feature data, a static-activity identification model for identification of plural static-activity patterns;
a first determination step of determining, based on the dynamic/static activity identification model and the second feature data, whether the subject is involved in a dynamic activity or in a static activity in the second predetermined period;
a second determination step of determining, based on the dynamic-activity identification model and the second feature data, a dynamic-activity pattern of the subject in the second predetermined period;
a third determination step of determining, based on the static-activity identification model and the second feature data, a static-activity pattern of the subject in the second predetermined period;
an identification step of identifying a posture and an activity of the subject in the second predetermined period, by combining together results of the determination in the first, second, and third determination steps; and
a generating step of generating correspondence information associating between the posture and activity identified in the identification step and biological signal information of the subject in the second predetermined period.

10. A non-transitory computer-readable recording medium having stored therein a sequential posture identification program that causes a computer to execute:
a reception process of receiving respectively, from an acceleration information measurement unit and a biological signal information measurement unit that are provided in a wearable device that is configured to be attached to a trunk of a subject, acceleration information on motion of the subject whom the wearable device is attached to, and biological signal information of the subject;
a feature data extraction process of extracting, from the acceleration information and the biological signal information, first feature data corresponding to a first predetermined period and second feature data corresponding to a second predetermined period;
a first generation process of generating, by machine learning based on the first feature data, a dynamic/static activity identification model for identification of whether the subject is involved in a dynamic activity or in a static activity;
a second generation process of generating, by machine learning based on the first feature data, a dynamic-activity identification model for identification of plural dynamic-activity patterns;
a third generation process of generating, by machine learning based on the first feature data, a static-activity identification model for identification of plural static-activity patterns;
a first determination process of determining, based on the dynamic/static activity identification model and the second feature data, whether the subject is involved in a dynamic activity or in a static activity in the second predetermined period;
a second determination process of determining, based on the dynamic-activity identification model and the second feature data, a dynamic-activity pattern of the subject in the second predetermined period;
a third determination process of determining, based on the static-activity identification model and the second feature data, a static-activity pattern of the subject in the second predetermined period;
an identification process of identifying a posture and an activity of the subject in the second predetermined period, by combining together results of the determination in the first, second, and third determination processes; and
a generating process of generating correspondence information associating between the posture and activity identified in the identification process and biological signal information of the subject in the second predetermined period.

* * * * *